United States Patent
Ibrahim et al.

(10) Patent No.: US 12,060,358 B2
(45) Date of Patent: Aug. 13, 2024

(54) ORALLY BIOAVAILABLE, BRAIN-PENETRANT COMPOUND WITH SELECTIVITY FOR THE CANNABINOID TYPE 2 RECEPTOR WITH POTENTIAL USE TOWARDS VISCERAL PAIN MANAGEMENT AND NEURODEGENERATIVE DISORDERS

(71) Applicant: University of Mississippi, University, MS (US)

(72) Inventors: Mohamed Ali Mohamed Ali Ibrahim, Oxford, MS (US); Jason Richard Paris, Little Rock, AR (US); Larry Anthony Walker, Milan, TN (US); Abbas Gholipour Shilabin, Johnson City, TN (US); Meirambek Ospanov, Oxford, MS (US)

( * ) Notice: Subject to any disclaimer, the term of this patent is extended or adjusted under 35 U.S.C. 154(b) by 0 days.

(21) Appl. No.: 18/191,247

(22) Filed: Mar. 28, 2023

(65) Prior Publication Data

US 2023/0303581 A1  Sep. 28, 2023

Related U.S. Application Data

(60) Provisional application No. 63/324,392, filed on Mar. 28, 2022.

(51) Int. Cl.
C07D 487/04 (2006.01)
A61P 25/04 (2006.01)

(52) U.S. Cl.
CPC ............ *C07D 487/04* (2013.01); *A61P 25/04* (2018.01)

(58) Field of Classification Search
CPC ............................... C07D 487/04; A61P 25/04
See application file for complete search history.

(56) References Cited

U.S. PATENT DOCUMENTS 9,486,419 B2   11/2016   Navi-Goffer

OTHER PUBLICATIONS

Patani et al. Bioisosterism: A rational approach in Drug design, Chem. Rev. 96, 3147-3176. (Year: 1996).*
Mingle et al. First in class (S,E)-11-[2-(arylmethylene)hydrazono]-PBD analogs as selective CB2 modulators targeting neurodegenerative disorders, Medicinal Chemistry Research, 30, 98-108. (Year: 2021).*
Sheridan, The Most Common Chemical Replacements in Drug-Like Compounds, J. Chem. Inf. Comput. Sci. , 42, 103-108. (Year: 2002).*
Ahn K, McKinney MK, Cravatt BF. "Enzymatic pathways that regulate endocannabinoid signaling in the nervous system." Chem Rev. 2008;108:1687-707.
Aso E, Andres-Benito P, Carmona M, Maldonado R, Ferrer I. "Cannabinoid receptor 2 participates in amyloid-beta processing in a mouse model of Alzheimer's disease but plays a minor role in the therapeutic properties of a cannabis-based medicine." J Alz-heimers Dis. 2016;51:489-500.
Aso E, Ferrer I. "Cannabinoids for treatment of Alzheimer's disease: moving toward the clinic." Front Pharm. 2014;5:37.
Aso E, Juves S, Maldonado R, Ferrer I. "CB2 cannabinoid receptor agonist ameliorates Alzheimer-like phenotype in AbetaPP/PS1 mice. J Alzheimers Dis." 2013;35:847-58.
Beltramo, M.; Bernardini, N.; Bertorelli, R.; Campanella, M.; Nicolussi, E.; Fredduzzi, S.; Reggiani, A. "CB2 receptor-mediated antihyperalgesia: Possible direct involvement of neural mechanisms. Eur. J. Neurosci." 2006, 23, 1530-1538.
Brettschneider, J.; Tredici, K.D.; Lee, V.M.; Trojanowski, J.Q. "Spreading of pathology in neurodegenerative diseases: A focus on human studies." Nat. Rev. Neurosci. 2015, 16, 109-120.

(Continued)

*Primary Examiner* — Matthew P Coughlin
*Assistant Examiner* — Meghan C Heasley
(74) *Attorney, Agent, or Firm* — Thomas | Horstemeyer, LLP

(57) ABSTRACT

The disclosure relates to compounds of Formula I, methods of making same, pharmaceutical compositions including same, and methods of treating pain and neurological disorders using same:

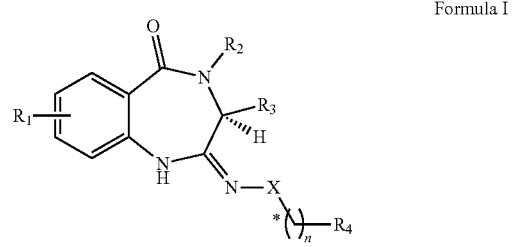

Formula I wherein $R_1$ is hydrogen, halogen, hydroxy, substituted or unsubstituted alkyl, substituted or unsubstituted alkoxy, aryl, nitro, or cyano;

wherein $R_2$ and $R_3$ are independently hydrogen, halogen, aryl, or substituted or unsubstituted alkyl, or wherein $R_2$ and $R_3$ are connected to form an alkyl chain;

wherein $R_4$ is a substituted or unsubstituted aryl or heteroaryl group having from 5 to 10 members;

wherein X is O, S, N, NH, CH, $CH_2$, or CO;

wherein n is from 0 to 10;

and wherein the bond indicated by * is a double bond or a single bond based on a valence of X.

The compounds selectively bind to CB2, can penetrate the blood brain barrier, and have a half-life of 20 hours or greater.

19 Claims, 5 Drawing Sheets

(56) References Cited

OTHER PUBLICATIONS

Cipolla, L.; Araújo, A.C.; Airoldi, C.; Bini, D. Pyrrolo "[2,1-c][1,4]benzodiazepine as a scaffold for the design and synthesis of anti-tumour drugs." Anticancer Agents Med. Chem. 2009, 9, 1-31.
Contino M, Capparelli E, Colabufo NA, Bush AI. "Editorial: the CB2 Cannabinoid System: a new strategy in neurodegenerative disorder and neuroinflammation." Front Neurosci. 2017;11:196.
Dean, B.; Sundram, S.; Bradbury, R.; Scarr, E.; Copolov, D. "Studies on [3H]CP-55940 binding in the human central nervous system: Regional specific changes in density of cannabinoid-1 receptors associated with schizophrenia and cannabis use." Neuroscience 2001, 103, 9-15.
Dhopeshwarkar A, Mackie K. "CB2 Cannabinoid receptors as a therapeutic target-what does the future hold?" Mol Pharm. 2014;86:430-7.
El-Shaheny R, Radwan M, Yamada K, El-Maghrabey M. "Estimation of nizatidine gastric nitrosatability and product toxicity via an integrated approach combining HILIC, in silico toxicology, and molecular docking." J Food Drug Anal. 2019;27:915-25.
El-Shaheny R, Radwan MO, Belal F, Yamada K. "Pentabromobenzyl-RP versus triazole-HILIC columns for separation of the polar basic analytes famotidine and famotidone: LC method development combined with in silico tools to follow the potential consequences of famotidine gastric instability." J Pharm Biomed Anal. 2020;18:113305.
Gao, H.M.; Hong, J.S. "Why neurodegenerative diseases are progressive: Uncontrolled inflammation drives disease progression." Trends Immunol. 2008, 29, 357-365.
Griffn G, Wray EJ, Tao Q, McAllister SD, Rorrer WK, Aung MM, et al. "Evaluation of the cannabinoid CB2 receptor-selective antagonist SR144528: further evidence for cannabinoid CB2 receptor absence in the rat central nervous system." Eur J Pharm. 1999;377:117-25.
Hebert, L.E.; Weuve, J.; Scherr, P.A.; Evans, D.A. "Alzheimer disease in the United States (2010-2050) estimated using the 2010 census." Neurology 2013, 80, 1778-1783.
Hua T, Vemuri K, Nikas SP, Laprairie RB, Wu Y, Qu L, et al. "Crystal structures of agonist-bound human cannabinoid receptor CB1." Nature. 2017;547:468-71.
Jayant, S.; Sharma, B.M.; Bansal, R.; Sharma, B. "Pharmacological benefits of selective modulation of cannabinoid receptor type 2 (CB2) in experimental Alzheimer's disease." Pharmacol. Biochem. Behav. 2016, 140, 39-50.
Khan N, Halim SA, Khan W, Zafar SK, Ul-Haq Z. "In-silico designing and characterization of binding modes of two novel inhibitors for CB1 receptor against obesity by classical 3D-QSAR approach." J Mol Graph Model. 2019;1:199-214.
Klein, T.W. "Cannabinoid-based drugs as anti-inflammatory therapeutics." Nat. Rev. Immunol. 2005, 5, 400-411.
Kumar KK, Shalev-Benami M, Robertson MJ, Hu H, Banister SD, Hollingsworth SA, et al. "Structure of a signaling cannabinoid receptor 1-G protein complex." Cell. 2019;176:448-58.
Lange JH, Coolen HK, Van Stuivenberg HH, Dijksman JA, Her-Remans AH, Ronken E, et al. "Synthesis, biological properties, and molecular modeling investigations of novel 3,4-diarylpyrazolines as potent and selective CB1 cannabinoid receptor antagonists." J Med Chem. 2004;47:627-43.
Li, X.; Hua, T.; Vemuri, K.; Ho, J.H.; Wu, Y.; Wu, L.; Popov, P.; Benchama, O.; Zvonok, N.; Qu, L.; et al. "Crystal structure of the human cannabinoid receptor CB2." Cell 2019, 176, 459-467.
Lynn AB, Herkenham M. "Localization of cannabinoid receptors and nonsaturable high-density cannabinoid binding sites in peripheral tissues of the rat: implications for receptor- mediated immune mod-ulation by cannabinoids." J Pharm Exp Ther. 1994;268:1612-23.

Martin-Moreno AM, Brera B, Spuch C, Carro E, Garcia-Garcia L, Delgado M, et al. "Prolonged oral cannabinoid administration prevents neuroinflammation, lowers beta-amyloid levels and improves cognitive performance in Tg APP 2576 mice." J Neu-roinflamm. 2012;9:8.
McPartland, J.M. "Phylogenomic and chemotaxonomic analysis of the endocannabinoid system." Brain Res. Rev. 2004, 45, 18-29.
Mingle, D.; Ospanov, M.; Radwan, M.O.; Ashpole, N.; Otsuka, M.; Ross, S.A.; Walker, L.; Shilabin, A. G.; Ibrahim, M.A. "First in Class (S,E)-11-[2-(Arylmethylene)Hydrazono]-PBD Analogs as Selective CB2 Modulators Targeting Neurodegenerative Disorders." Med. Chem. Res. 2020, 1-11.
Mukhopadhyay, S.; Das, S.; Williams, E.A.; Moore, D.; Jones, J.D.; Zahm, D.S.; Ndengele, M.M.; Lechner, A.J.; Howlett, A.C. "Lypopolysaccharide and cyclic AMP regulation of CB2 cannabinoid receptor levels in rat brain and mouse RAW 264.7 macrophages." J. Neuroimmunol. 2006, 181, 82-92.
Nakagawa, Y.; Chiba, K. "Role of microglial m1/m2 polarization in relapse and remission of psychiatric disorders and diseases." Pharmaceuticals 2014, 7, 1028-1048.
Nguyen, T., Thomas, B.F. and Zhang, Y., 2019. "Overcoming the psychiatric side effects of the cannabinoid CB1 receptor antagonists: current approaches for therapeutics development." Current topics in medicinal chemistry, 19(16), pp. 1418-1435.
Ospanov, M.; Sulochana, S.P., Paris, J.J., Rimoldi, J.M., Ashpole, N., Walker, L., Ross, S.A., Shilabin, A.G. and Ibrahim, M.A., 2022. "Identification of an Orally Bioavailable, Brain-Penetrant Compound with Selectivity for the Cannabinoid Type 2 Receptor." Molecules, 27(2), p. 509.
Pacher P, Bátkai S, Kunos G. "The Endocannabinoid System as an Emerging Target of Pharmacotherapy." Pharm Rev. 2006;58:389-462.
Papahatjis DP, Nikas SP, Kourouli T, Chari R, Xu W, Pertwee RG, et al. "Pharmacophoric requirements for the cannabinoid side chain." Probing the cannabinoid receptor subsite at C1'. J Med Chem. 2003;46:3221-9.
Pertwee RG, Howlett AC, Abood ME, Alexander SP, Di Marzo V, Elphick MR, et al. "International Union of Basic and Clinical Pharmacology. LXXIX. Cannabinoid receptors and their ligands." Beyond CB1 and CB2. Pharm Rev. 2010;62:588-631.
Porter RF, Szczesniak AM, Toguri JT, Gebremeskel S, Johnston B, Lehmann C, et al. "Selective Cannabinoid 2 Receptor Agonists as Potential Therapeutic Drugs for the Treatment of Endotoxin-Induced Uveitis." Molecules. 2019;24:3338.
Salami, S.A., Martinelli, F., Giovino, A., Bachari, A., Arad, N. and Mantri, N., 2020. "It is our turn to get cannabis high: Put cannabinoids in food and health baskets." Molecules, 25(18), p. 4036.
Schmidt, A.; Shilabin, A.G.; Namyslo, J.C.; Nieger, M.; Hemmen, S. "Pyrimidine-annulated Pyrrolobenzodiazepines." A New Ring System Related to Aspergillus Alkaloids. Eur. J. Org. Chem. 2005, 1781-1789.
Schmidt, A.; Shilabin, A.G.; Nieger, M. "Syntheses and tautomerization of amino-substituted and pyrimidine-annulated pyrrolobenzodiazepines." Heterocycles 2005, 65, 625-632.
Shao Z, Yin J, Chapman K, Grzemska M, Clark L, Wang J, et al. "High-resolution crystal structure of the human CB1 cannabinoid receptor." Nature. 2016;540:602-6.
Sonkusare SK, Kaul CL, Ramarao P. "Dementia of Alzheimer's disease and other neurodegenerative disorders—memantine, a new hope." Pharm Res. 2005;51:1-7.
Stempel, A.V.; Stumpf, A.; Zhang, H.Y.; Ozdogan, T.; Pannasch, U.; Theis, A.K.; Otte, D.M.; Wojtalla, A.; Racz, I.; Ponomarenko, A.; et al. "Cannabinoid type 2 receptors mediate a cell type-specific plasticity in the hippocampus." Neuron 2016, 90, 795-809.
Wu, J.; Bie, B.; Yang, H.; Xu, J.J.; Brown, D.L.; Naguib, M. "Activation of the CB2 receptor system reverses amyloid-induced memory deficiency." Neurobiol. Aging 2013, 34, 791-804.

\* cited by examiner

ORALLY BIOAVAILABLE, BRAIN-PENETRANT COMPOUND WITH SELECTIVITY FOR THE CANNABINOID TYPE 2 RECEPTOR WITH POTENTIAL USE TOWARDS VISCERAL PAIN MANAGEMENT AND NEURODEGENERATIVE DISORDERS

CROSS-REFERENCE TO RELATED APPLICATIONS

This application claims the benefit of U.S. Provisional Application No. 63/324,392, filed on Mar. 28, 2022, which is incorporated herein by reference in its entirety.

STATEMENT REGARDING FEDERALLY SPONSORED RESEARCH OR DEVELOPMENT

This invention was made with government support under grant number P30GM122733-01A1, awarded by the National Institutes of Health. The government has certain rights in the invention.

BACKGROUND

Cannabinoids are a class of secondary metabolites from plants in the Cannabis family (i.e., C. sativa, C. indica, and C. ruderalis). Two subtypes of cannabinoid receptors can be found in the human body. These are known as CB1 and CB2, both of which are G protein-coupled receptors. CB1 and CB2 are expressed in different locations in the body, although both have been found in the brain. CB1 is implicated in several signaling pathways such as, for example, GABA-mediated neurotransmission, while CB2 is involved in pain perception and relief, among other functions.

Synthetic or semi-synthetic compounds interacting with CB1 and/or CB2 are believed to be effective treatments for numerous diseases and medical conditions including, but not limited to, neurological and neurodegenerative disorders, pain disorders, inflammation-related disorders, and other conditions. However, most studies have focused on the effects of $\Delta^9$-tetrahydrocannabinol (THC), cannabidiol (CBD), and combinations thereof.

Neurodegenerative disorders are a widespread cause of morbidity and mortality worldwide, characterized by the slow, progressive damage/loss of neurons in the central nervous system (CNS), which is associated with deficits in function (e.g., movement, memory, cognition) that are related to the affected CNS region(s). The progression of many neurodegenerative diseases is thought to be driven by the template-directed misfolding, seeded aggregation, and cell-cell transmission of characteristic disease-related proteins, leading to the consecutive spreading of pathological protein aggregates. Modulating the activity of endocannabinoids (ECB) has held therapeutic promise for treating a wide range of diseases associated with inflammation and oxidative stress. The cannabinoid receptors subtype 2 (CB2), which were identified molecularly in 1993, have been the subject of considerable attention, primarily due to their promising anti-inflammatory potential without the adverse psychotropic effects more commonly associated with CB1 receptor-based therapies. Many studies have further corroborated the in vivo link between chronic neuroinflammation and CB2 upregulation in animal models of pain and inflammation. These studies raise the possible logical connection between CB2 receptors and immunological function. Activation of CB2 receptors by ligands favors a range of receptor conformations that can affect different signaling pathways.

CB2 receptors are also emerging as novel targets for the development of new therapeutic approaches to Alzheimer's disease, since CB2 is primarily localized in macrophages in the peripheral immune system as well as being overexpressed in microglia in response to neuroinflammation. Since Alzheimer's disease currently represents at least 70% of dementia cases, and is a leading cause of death in the United states, therapies useful in treating the neuroinflammation associated with this disease would be highly desirable.

CB2 is a crucial target for many neurological and pain disorders, since targeting CB1 often has serious side effects including, but not limited to, addiction. Many CB2-targeting compounds developed thus far have a limited ability to cross the blood brain barrier (BBB) and, of those, few have a pharmacologically-useful half time. Additionally, known CB2-targeting compounds typically have low oral bioavailability.

Despite advances in synthetic cannabinoid research, there is still a scarcity of compounds that are potent and efficacious at relieving pain and other neurological symptoms while also being selective for CB2, being orally bioavailable, and having a long half time in vivo. These needs and other needs are satisfied by the present disclosure.

SUMMARY

In accordance with the purpose(s) of the present disclosure, as embodied and broadly described herein, the disclosure, in one aspect, relates to compounds of Formula I, methods of making the same, pharmaceutical compositions comprising the same, and methods of treating pain and neurological disorders using the same:

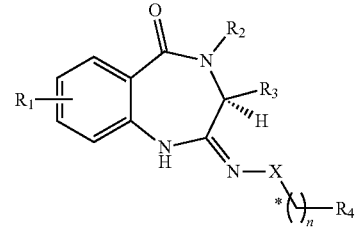

Formula I wherein $R_1$ is selected from hydrogen, halogen, hydroxy, substituted or unsubstituted $C_1$-$C_{10}$ alkyl, substituted or unsubstituted $C_1$-$C_{10}$ alkoxy, aryl, nitro, cyano, or any combination thereof;

wherein $R_2$ and $R_3$ are independently selected from hydrogen, halogen, aryl, substituted or unsubstituted $C_1$-$C_{10}$ alkyl, or any combination thereof, or wherein $R_2$ and $R_3$ are connected to form a $C_2$-$C_{10}$ alkyl chain;

wherein $R_4$ is a substituted or unsubstituted aryl or heteroaryl group having from 5 to 10 members;

wherein X is selected from O, S, N, NH, CH, $CH_2$, CO, or any combination thereof;

wherein n is from 0 to 10;

and wherein the bond indicated by * is a double bond or a single bond based on a valence of X.

In one aspect, the compounds selectively bind to CB2 and are able to penetrate the blood brain barrier as well as having an in vivo half-life of 20 hours or greater.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

(FIG. 3B).

Figure 1:
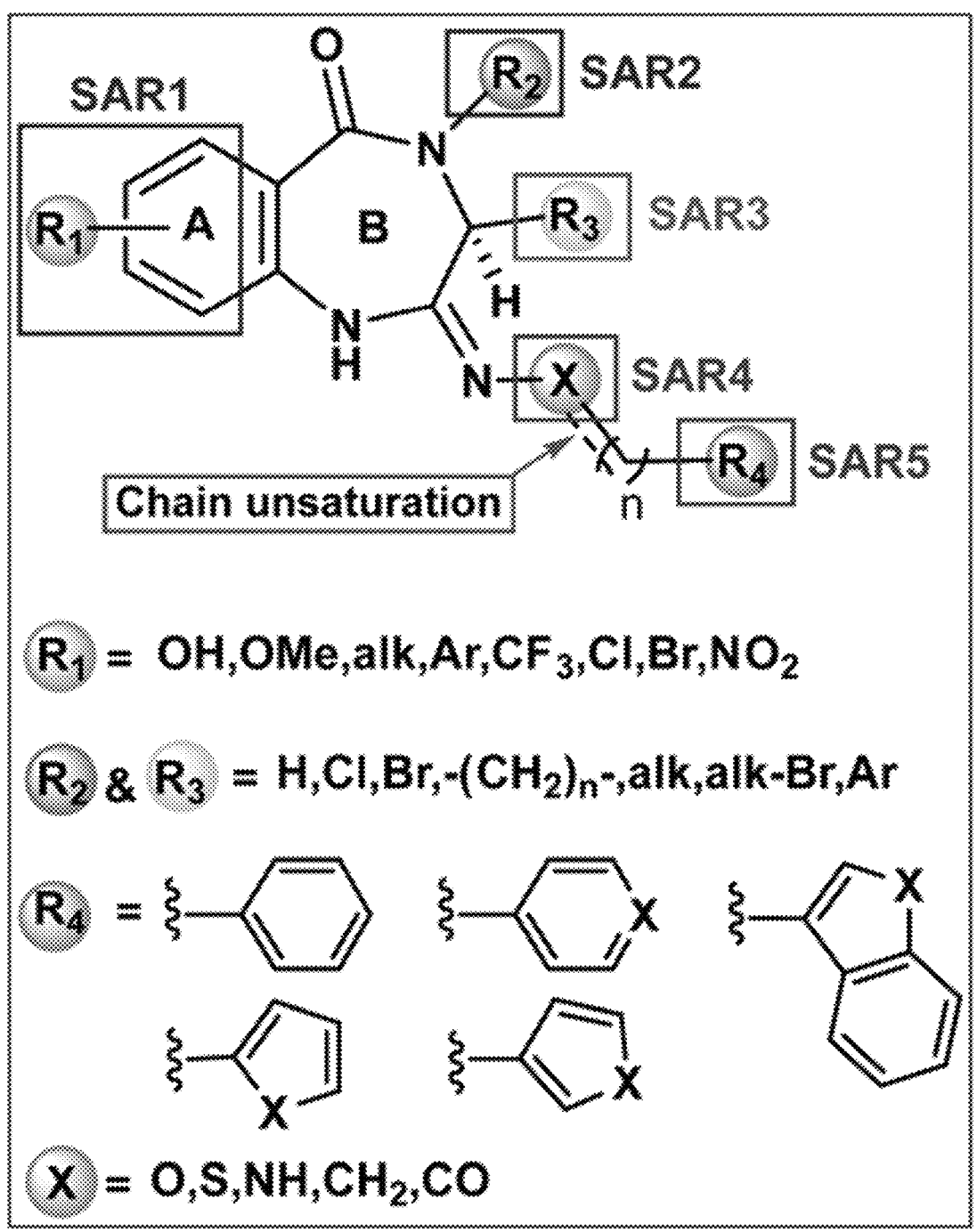
FIG. 1 shows structures of exemplary compounds according to one embodiment of the present disclosure.
Figure 2A:
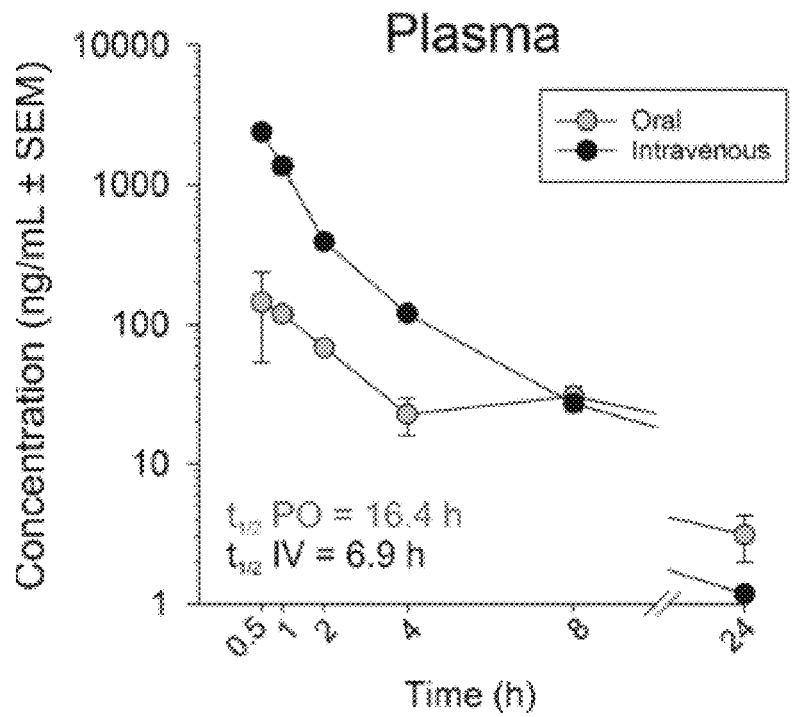
FIGS. 2A-2D show pharmacokinetic profiles of compound 4k in plasma (FIG. 2A), brain (FIG. 2B), liver (FIG. 2C), and kidney (FIG. 2D) of CD1 mice following intravenous and oral dosing of 4 k to mice at 5 mg/kg.
Figure 2B:
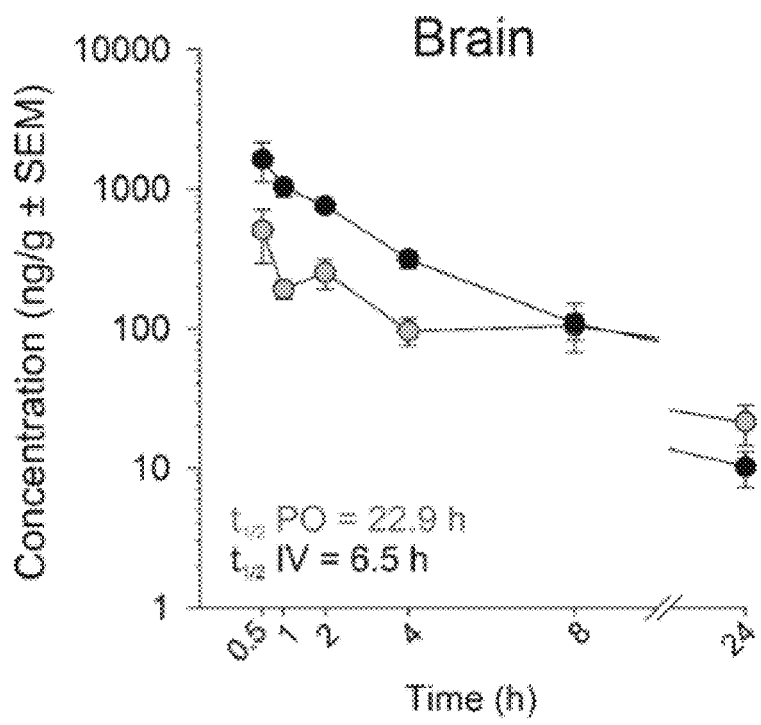
Figure 2C:
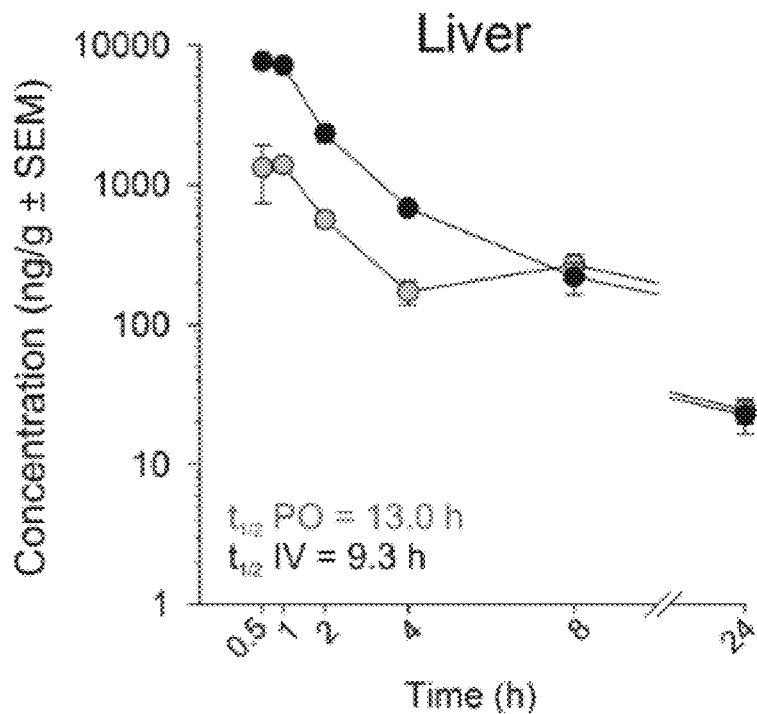
Figure 2D:
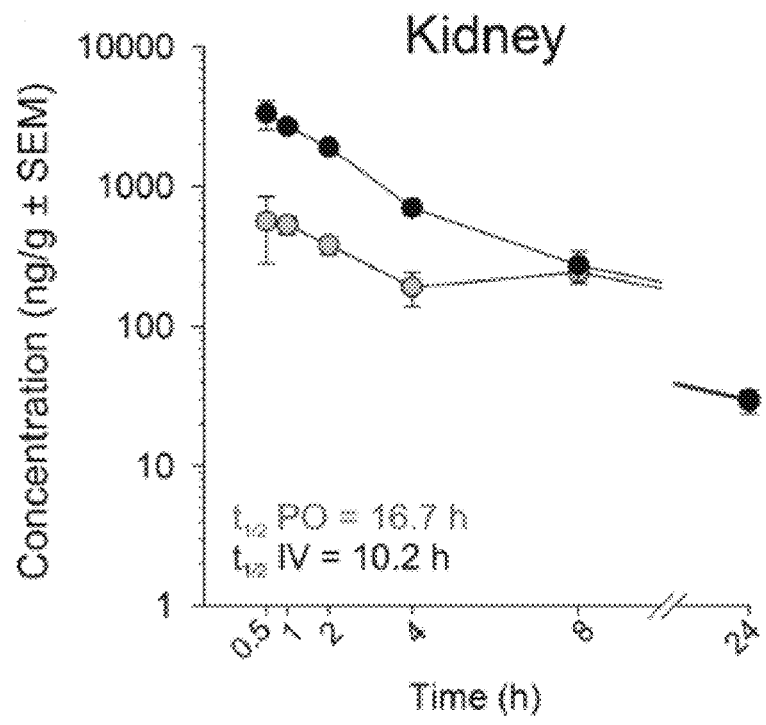

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are compounds useful for the treatment of pain and neurological disorders. The compounds are orally bioavailable with a long half-life and are equal to or better at treating pain compared to common opioids such as, for example, oxycodone. In an aspect, the compounds can cross the blood-brain barrier and are selective for CB2 over CB1. In a further aspect, the compounds are non-addictive and/or do not have the psychoactive effects associated with known cannabinoids and cannabinoid-like molecules and compositions. Also disclosed are methods for treating pain and neurological disorders using the compounds.

In one aspect, disclosed herein is a compound having a structure of Formula I:

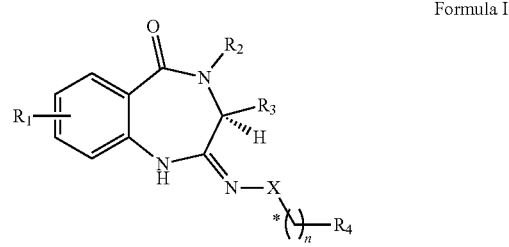

Formula I wherein $R_1$ is selected from hydrogen, halogen, hydroxy, substituted or unsubstituted $C_1$-$C_{10}$ alkyl, substituted or unsubstituted $C_1$-$C_{10}$ alkoxy, aryl, nitro, cyano, or any combination thereof;

wherein $R_2$ and $R_3$ are independently selected from hydrogen, halogen, aryl, substituted or unsubstituted $C_1$-$C_{10}$ alkyl, or any combination thereof, or wherein $R_2$ and $R_3$ are connected to form a $C_2$-$C_{10}$ alkyl chain;

wherein $R_4$ is a substituted or unsubstituted aryl or heteroaryl group having from 5 to 10 members;

wherein X is selected from O, S, N, NH, CH, $CH_2$, CO, or any combination thereof;

wherein n is from 0 to 10;

and wherein the bond indicated by * is a double bond or a single bond based on a valence of X.

In another aspect, the compound can be selected from Formula Ia or Formula Ib:

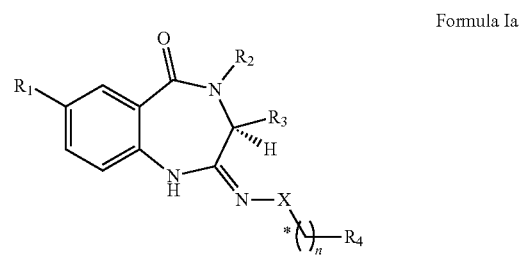

Formula Ia

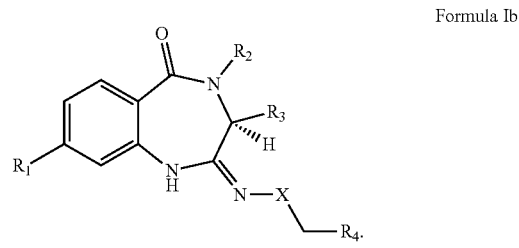

Formula Ib

In one aspect, $R_1$ is selected from H, bromine, chlorine, or any combination thereof, and in another aspect, $R_2$ and $R_3$ are connected to form a $C_2$-$C_{10}$ alkyl chain. In still another aspect, the compound can have Formula Ic:

Formula Ic
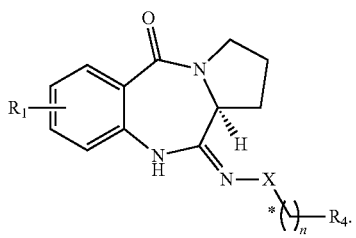
In any of these aspects, X can be N and the bond indicated by * can be a double bond. In another aspect, n is 1. In a further aspect, $R_4$ can be selected from C
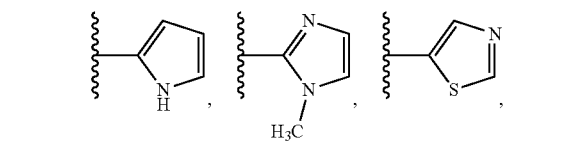
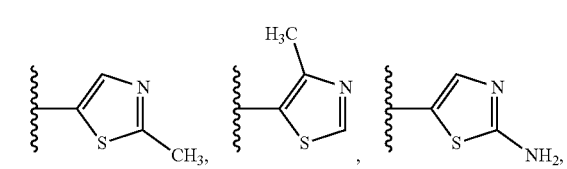
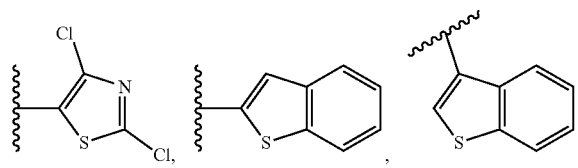
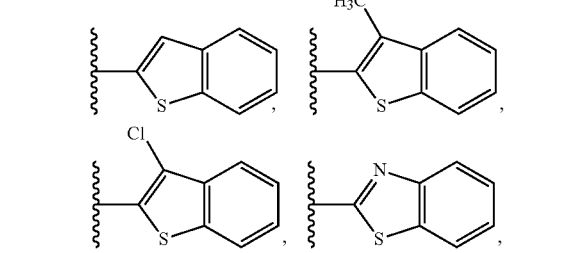
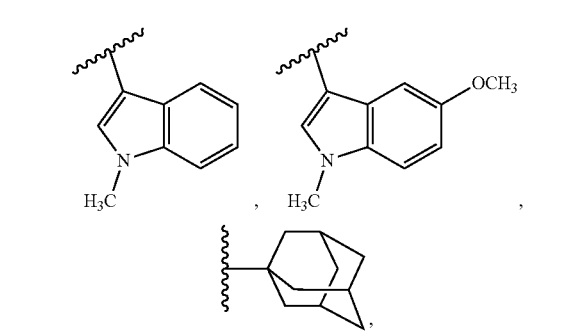
or any combination thereof.
In a further aspect, the compound has the structure
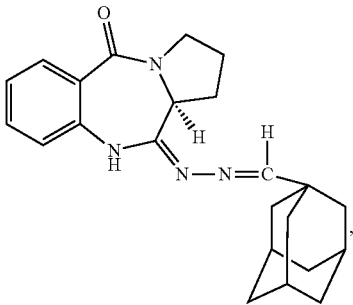
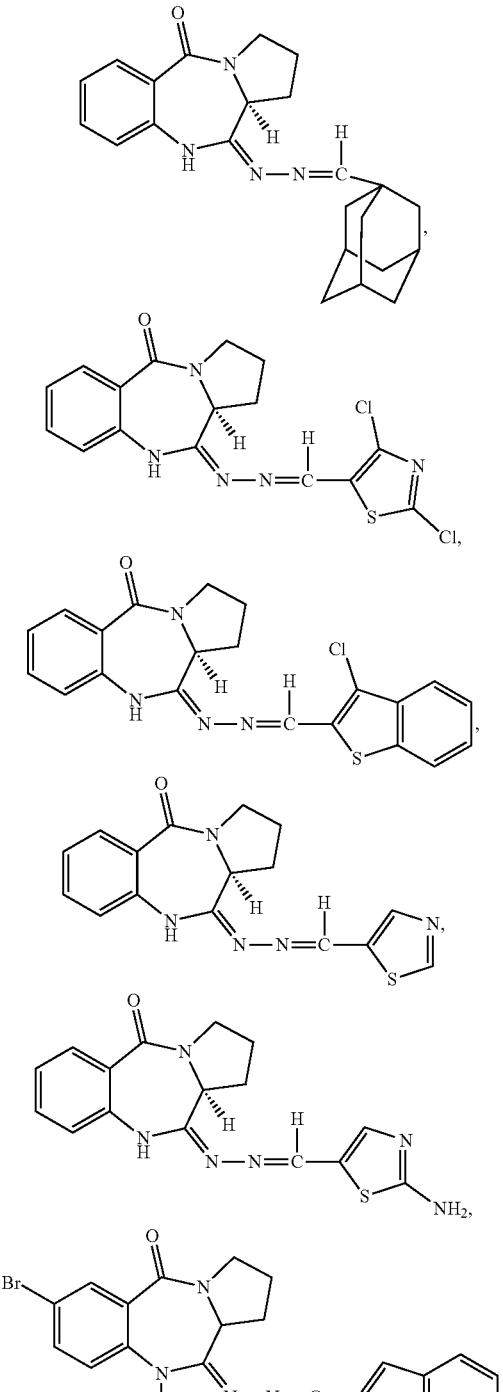
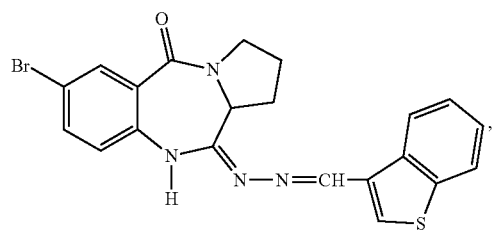

-continued

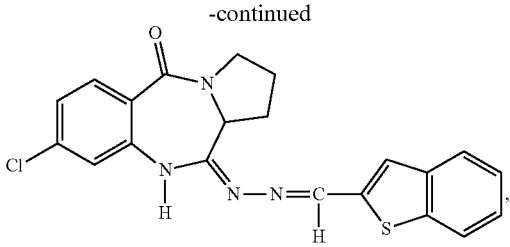

or any combination thereof.

In still another aspect, also disclosed herein are pharmaceutical compositions including the disclosed compounds or pharmaceutically acceptable salts thereof.

In one aspect, disclosed herein is a method for treating pain or a neurological disorder, the method including administering a pharmaceutically effective amount of one or more of the disclosed compounds or pharmaceutical compositions to a subject. In a further aspect, the subject can be a mammal such as, for example, a human or other primate, mouse, rat, guinea pig, dog, cat, goat, pig, cattle, horse, or sheep.

In a further aspect, the neurological disorder can be Alzheimer's disease, Parkinson's disease, multiple sclerosis, or any combination thereof.

In another aspect, the pain can be pain resulting from an injury, pain resulting from a pain disorder, post-surgical pain, pain resulting from an infection, or any combination thereof. In one aspect, the pain can be acute or chronic. In another aspect, the pain disorder can be selected from, but is not limited to, rheumatoid arthritis, osteoarthritis, migraine or other headache, cancer pain, pain in scar tissue, fibromyalgia, neurogenic pain, back pain, chronic fatigue syndrome, endometriosis, interstitial cystitis, vulvodynia, temporomandibular disorder, or any combination thereof.

In some aspects, the compound or pharmaceutical composition is administered orally. In an alternative aspect, the compound or pharmaceutical composition can be administered intravenously. In either of these aspects, the composition can be administered at a dosage of from around 2.5 to around 10 mg per kg of subject body weight, or at about 2.5, 3, 3.5, 4, 4.5, 5, 5.5, 6, 6.5, 7, 7.5, 8, 8.5, 9, 9.5, or about 10 mg per kg of subject body weight. In another aspect, the compound penetrates the blood-brain barrier. In one aspect, the compound has an in vivo half-life of greater than about 20 hours, or of 20, 20.5, 21, 21.5, or about 22 hours, or a combination of any of the foregoing values, or a range encompassing any of the foregoing values. In one aspect, the compound or pharmaceutical composition can be administered once, or can be administered once or twice per day for a period of up to two weeks, or can be administered daily as needed for chronic pain and neurological disorders. In any of these aspects, the compound selectively binds to CB2. In a further aspect, the compound has a Ki for CB2 of less than about 150 nM, or less than about 140, 130, 120, 110, or about 100 nM, or a combination of any of the foregoing values, or a range encompassing any of the foregoing values. In another aspect, the compound is at least about 1.5 times more selective for CB2 over CB1, or at least about 2 times more selective for CB2 over CB1. Further in this aspect, selectivity can be measured by any means known in the art, such as, for example, competitive binding assays, or ligand displacement assays, wherein the compound is about 1.5 times or about 2 times more likely to displace a ligand from CB2 than to displace the same ligand from CB1. In any of these aspects, administering the compound to the subject does not result in the subject becoming addicted to the compound. Furthermore, in an aspect, the compound does not cause psychoactive effects.

In any of these aspects, the disclosed method can be performed in conjunction with another method for pain treatment including, but not limited to, acupuncture, use of one or more analgesics or non-steroidal anti-inflammatory drugs or opioids, use of an anticonvulsant or antidepressant, an anti-inflammatory diet, use of a beta-blocker, biofeedback, injections with botulinum toxin, calcitonin gene-related peptide monoclonal antibodies, chiropractic care, cognitive-behavioral therapy, counseling, relaxation and mindfulness techniques, physical therapy, radiofrequency ablation, surgery, a topical pain cream or gel, electrical stimulation (such as, for example, transcutaneous electrical stimulation or TENS, peripheral nerve stimulation, spinal cord stimulation, or deep brain stimulation), exercise, hypnosis, steroid injections or other steroid treatment, injections of local anesthetic, laser therapy, treatment with medical *cannabis*, and/or treatment with muscle relaxants, anxiolytics, nerve blocks, or any combination thereof.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by," "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a compound," "a pharmaceutical composition," or "an excipient," includes, but is not limited to, mixtures or combinations of two or more such compounds, pharmaceutical compositions, or excipients, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a disclosed compound refers to an amount that is sufficient to achieve the desired improvement in the property modulated by the formulation component, e.g. achieving the desired level of pain control. The specific level in terms of wt % in a composition required as an effective amount will depend upon a variety of factors including the type of pain, dosage frequency and/or amount, method of administration of the compound, excipients, and the like.

As used herein, the terms "optional" or "optionally" means that the subsequently described event or circumstance can or cannot occur, and that the description includes instances where said event or circumstance occurs and instances where it does not.

Unless otherwise specified, pressures referred to herein are based on atmospheric pressure (i.e. one atmosphere).

Pharmaceutical Compositions

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravitreal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In one aspect, the pharmaceutical compositions disclosed herein can be administered orally. In a further aspect, oral administration can be conducted at the patient's home and requires no specialized training which can, in turn, increase patient compliance with medication instructions.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as pain and/or symptoms of a neurological condition. The effect can be therapeutic in terms of a partial or complete cure of a disease, condition, symptom or adverse effect attributed to the disease, disorder, or condition. The term "treatment" as used herein can include any treatment of pain and/or neurological conditions in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

In various aspects, it is contemplated herein that the disclosed compounds further comprise their biosteric equivalents. The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience; New York, 1970, 64-80; (ii) Burger, A.; "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", *Perspect. Drug Discovery Des.* 1998, 9/10/11, 213-224; (v) Koyanagi T, Haga T, "Bioisosterism in agrochemicals", *ACS Symp. Ser.* 1995, 584, 15-24; (vi) Kubinyi H, "Molecular similarities. Part 1. Chemical structure and biological activity", *Pharm. Unserer Zeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J, "Bioisosteric approach in the design of new dopaminergic/serotonergic ligands", *Curr. Med. Chem.* 1998, 5, 493-512 (x) Thornber C W, "Isosterism and molecular modification in drug design", *Chem. Soc. Rev.* 1979, 8, 563-80.

In further aspects, bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

In various aspects, it is contemplated herein that the disclosed compounds further comprise their isotopically-labelled or isotopically-substituted variants, i.e., compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

In various aspects, the disclosed compounds can be in the form of a co-crystal. The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Preferred co-crystals include p-toluenesulfonic acid and benzenesulfonic acid.

The term "pharmaceutically acceptable co-crystal" means one that is compatible with the other ingredients of the formulation and not deleterious to the recipient thereof.

In a further aspect, the disclosed compounds can be isolated as solvates and, in particular, as hydrates of a disclosed compound, which can be obtained, for example, by crystallization from a solvent or from aqueous solution. In this connection, one, two, three or any arbitrary number of solvate or water molecules can combine with the compounds according to the invention to form solvates and hydrates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulfuric acid and phosphoric acid and such organic acids as oxalic acid, maleic acid, succinic acid and citric acid. In a further aspect, salts further include, but are not limited, to the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e., 1,1'-methylene-bis-(2-hydroxy-3-naphthoate)) salts. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids that can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Oral Dosage Forms

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example Eudragit® RS), copolymerizates of acrylic and methacrylic acid esters and trimethyl ammonium methacrylate (for example Eudragit® RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monoocatanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulfoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

Dosage and Packaging of Pharmaceutical Compositions

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require modulation of CB2 activity an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for modulating CB2 activity (e.g., treatment of one or more pain disorders) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and a CB2-binding compound. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional analgesic therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

Chemical Definitions

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "alkanediyl" as used herein, refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$— (methylene), —$CH_2CH_2$—, —$CH_2C(CH_3)_2CH_2$—, and —$CH_2CH_2CH_2$— are non-limiting examples of alkanediyl groups.

The terms "alkoxy" and "alkoxyl" as used herein to refer to an alkyl or cycloalkyl group bonded through an ether linkage; that is, an "alkoxy" group can be defined as -$OA^1$ where $A^1$ is alkyl or cycloalkyl as defined above. "Alkoxy" also includes polymers of alkoxy groups as just described; that is, an alkoxy can be a polyether such as -$OA^1$-$OA^2$ or -$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula -NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) and —N(-alkyl)$_2$, where alkyl is a described herein. Representative examples include, but are not limited to, methylamino group, ethylamino group, propylamino group, isopropylamino group, butylamino group, isobutylamino group, (sec-butyl)amino group, (tert-butyl) amino group, pentylamino group, isopentylamino group, (tert-pentyl)amino group, hexylamino group, dimethylamino group, diethylamino group, dipropylamino group, diisopropylamino group, dibutylamino group, diisobutylamino group, di(sec-butyl)amino group, di(tert-butyl) amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b] pyridazinyl, imidazo[1,2-a]pyrazinyl, benzo[c][1,2,5] thiadiazolyl, benzo[c][1,2,5]oxadiazolyl, and pyrido[2,3-b] pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $-N_3$.

The term "nitro" as used herein is represented by the formula $-NO_2$.

The term "nitrile" or "cyano" as used herein is represented by the formula —CN.

The term "silyl" as used herein is represented by the formula $-SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $-S(O)A^1$, $-S(O)_2A^1$, $-OS(O)_2A^1$, or $-OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $-S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," ... "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R°$; $-(CH_2)_{0-4}OR°$; $-O(CH_2)_{0-4}R°$, $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; —CH=CHPh, which may be substituted with $R°$; $-(CH_2)_{0-4}O(CH_2)_{0-1}$-pyridyl which may be substituted with $R°$; $-NO_2$; $-CN$; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-(CH_2)_{0-4}C(O)R°$; $-C(S)R°$; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; $-OC(O)(CH_2)_{0-4}SR-$, $SC(S)SR°$; $-(CH_2)_{0-4}SC(O)R°$; $-(CH_2)_{0-4}C(O)NR°_2$; $-C(S)NR°_2$; $-C(S)SR°$; $-(CH_2)_{0-4}OC(O)NR°_2$; $-C(O)N(OR°)R°$; $-C(O)C(O)R°$; $-C(O)CH_2C(O)R°$; $-C(NOR°)R°$; $-(CH_2)_{0-4}SSR°$; $-(CH_2)_{0-4}S(O)_2R°$; $-(CH_2)_{0-4}S(O)_2OR°$; $-(CH_2)_{0-4}OS(O)_2R°$; $-S(O)_2NR°_2$; $-(CH_2)_{0-4}S(O)R°$; $-N(R°)S(O)_2NR°_2$; $-N(R°)S(O)_2R°$; $-N(OR°)R°$; $-C(NH)NR°_2$; $-P(O)_2R°$; $-P(O)R°_2$; $-OP(O)R°_2$; $-OP(O)(OR°)_2$; $SiR°_3$; $-(C_{1-4}$ straight or branched alkylene)O—N(R°)_2$; or $-(C_{1-4}$ straight or branched alkylene)C(O)O—N(R°)_2$, wherein each $R°$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR—, —NH$_2$, —NHR—, —NR$^\circ$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

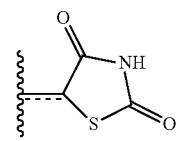

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkyl-carboxamide, dialkylcarboxamide, substituted dialkylcar-boxamide, alkylsulfonyl, alkylsulfinyl, thioalkyl, thiohaloal-kyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^{2}H$, $^{3}H$, $^{13}C$, $^{14}C$ $^{15}N$, $^{18}O$, $^{17}O$, $^{35}S$, $^{18}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

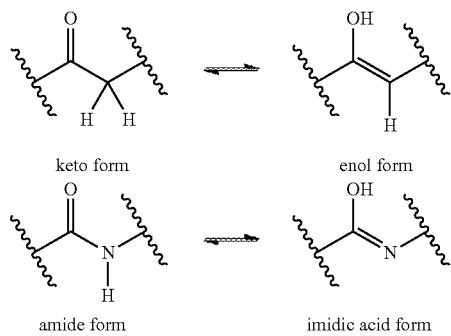

keto form    enol form
amide form   imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

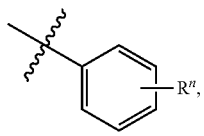

which is understood to be equivalent to a formula:

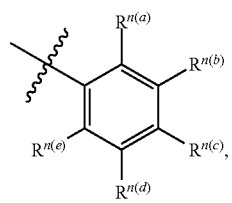

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Materials and Methods

General Experimental Procedures

The $^1$H and $^{13}$C NMR spectra were recorded in DMSO-$d_6$ and CDCl$_3$ on Bruker 400 and 500 MHz spectrometer operating at 400, 500 MHz for $^1$H and 100, 150 MHz for $^{13}$C NMR. Chemical shift (δ) values are presented in ppm and in reference to the residual solvent signals of DMSO-$d_6$ and CDCl$_3$ at 6H/6C 2.50/39.5 and 7.25/70.2, respectively. The coupling constants value (J) reported in Hz.

LC analysis was conducted using an Agilent 1100 HPLC system, RP-C18 column (150×4.6 mm; particle size 5 μm; Luna) with column oven temperature set at 25° C. and a gradient system of eluent water (A) and acetonitrile (B). The gradient condition was as follows: 0-2 min (5% B), 2-5 min (5% B→50% B), 5-10 min (50% B→100% B), 10-15 min (100% B). The flow rate of the solvent was 1.0 mL/min, and the injection volume was 25 μL. All analysis was carried out at wavelength of 254 nm with a run time of 15 min. HPLC-grade acetonitrile and water solvents were used. Acetic acid was added as a modifier to achieve a final concentration of 0.1% in each solvent.

Preparative HPLC purification was carried out using an Agilent 1100 HPLC system, RP-C18 column (250×10 mm; particle size 10 μm; Luna) with column oven temperature set at 25° C. and a gradient system of eluent water (A) and acetonitrile (B). The gradient condition was as follows: 0-2 min (5% B), 2-5 min (5% B→50% B), 5-10 min (50% B→100% B), 10-15 min (100% B). The flow rate of the solvent was 3.0 mL/min, and the injection volume was 25 μL. All analysis was carried out at wavelength of 254 nm with a run time of 15 min. HPLC-grade acetonitrile and water solvents were used. Acetic acid was added as a modifier to achieve a final concentration of 0.1% in each solvent.

Other common chromatographic techniques, such as thin layer chromatography (TLC) on precoated silica gel $G_{254}$ aluminum plates and silica gel flash column chromatography, were also engaged in the purification of the synthesized compounds.

Synthesis

General Method for Synthesis of (S,E)-11-[2-(Aryl-methylene)hydrazono]-pyrrolo [2,1-c][1,4] Benzodiazepines (4a-4q)

To a solution of 3 (230 mg, 1.0 mmol) in anhydrous methanol (10 mL) was added aldehyde (1.0 mmol). 3 Å molecular sieves (0.5 g) was also added and stirred at room temperature. Various modifications were used to obtain compounds 4a-4q.(Spectroscopic data for PBD analogs (4a-4q) and typical MRM chromatograms of 4k in plasma and tissues are available in Supplementary Materials)

(S,E)-11-[(1H-Pyrrol-2-yl)methylene)hydrazono]-pyrrolo[2,1-c][1,4] Benzodiazepine (4a)

Starting material pyrrole-2-carboxaldehyde (57.0 mg, 0.60 mmol) was used and the reaction mixture was stirred under nitrogen gas overnight for 15 h. Extraction was performed using chloroform/isopropanol (2:1) (3×20 mL), where the organic layers were dried over anhydrous Na$_2$SO$_4$. The solvent mixture was then removed in vacuo and washed with diethyl ether, filtered off, and dried to afford a yellow solid of 4a. Yield 114.0 mg (62.0%); $^1$H-NMR (400 MHz, DMSO-$d_6$): δ=1.95 (m, 3H), 2.78 (bd, 1H), 3.56 (m, 2H), 4.43 (bd, 1H, H-11a), 6.17 (s, 1H), 6.51 (s, 1H), 7.10 (s, 1H), 7.19 (m, 2H), 7.53 (t, J=8.0 Hz, 1H), 7.78 (d, J=8.0 Hz, 1H), 8.21 (s, 1H, CH), 9.52 (s, 1H, NH); $^{13}$C-NMR (100 MHz, DMSO-$d_6$): δ=23.4, 26.2, 47.3, 55.3 (C-11a), 109.9, 114.6, 121.9, 122.8, 123.3, 126.5, 128.9, 131.1, 132.6, 138.0, 147.1, 156.9, 165.5 (C=O).

(S,E)-11-[(1-Methyl-1H-imidazol-2-yl)methylene)hydrazono]-pyrrolo[2,1-c][1,4]Benzodiazepine (4b)

Starting material 1-methylimidazole-2-carboxaldehyde (95.8 mg, 0.87 mmol) was used and the reaction mixture was stirred under nitrogen gas overnight for 15 h. Extraction was performed using chloroform/isopropanol (2:1) (3×20 mL). The combined organic layers were dried over anhydrous Na$_2$SO$_4$. The solvent mixture was then removed in vacuo and washed with diethyl ether, filtered off, and dried to afford an off-white solid of 4b. Yield 182.0 mg (65.0%); $^1$H-NMR (400 MHz, DMSO-$d_6$): δ=1.98 (m, 3H), 2.81 (bd, 1H), 3.56 (m, 2H), 4.03 (s, 3H), 4.43 (bd, 1H, H-11a), 7.09 (s, 1H), 7.17 (m, 1H), 7.33 (d, J=8.0 Hz, 1H), 7.39 (s, 1H), 7.48 (bt, 1H), 7.77 (d, J=8.0 Hz, 1H), 8.30 (s, 1H, CH); $^{13}$C-NMR (100 MHz, DMSO-$d_6$): δ=23.3, 26.5, 35.7, 47.4, 55.3 (C-11a), 122.6, 123.7, 126.2, 126.6, 129.7, 130.8, 131.1, 132.4, 137.6, 142.3, 156.7, 165.3 (C=O).

(S,E)-11-[(Thiazol-5-ylmethylene)hydrazono]-pyrrolo[2,1-c][1,4] Benzodiazepine (4c)

Starting material 5-formylthiazole (56.6 mg, 0.60 mmol) was used and the reaction mixture was stirred under nitrogen gas overnight for 15 h. Extraction was performed using chloroform/isopropanol (2:1) (3×20 mL), where the organic layers were dried over anhydrous Na$_2$SO$_4$. The solvent mixture was then removed in vacuo and washed with diethyl ether, filtered off, and dried to afford a yellow solid of 4c. Yield 115.5 mg (71.0%); $^1$H-NMR (400 MHz, DMSO-$d_6$): δ=2.08 (m, 3H), 3.05 (bd, 1H), 3.59 (m, 2H), 4.49 (bd, 1H, H-11a), 7.19 (t, J=7.2 Hz, 1H), 7.37 (d, J=8.0 Hz, 1H), 7.48 (t, J=7.2 Hz, 1H), 7.76 (d, J=8.0 Hz, 1H), 8.36 (s, 1H), 8.43 (s, 1H), 9.26 (s, 1H, CH), 9.88 (s, 1H, NH); $^{13}$C-NMR (100 MHz, DMSO-d$_6$): δ=23.7, 26.5, 47.4, 55.8 (C-11a), 122.9, 123.8, 126.9, 127.8, 130.7, 132.4, 137.5, 144.7, 149.2, 158.2, 160.6, 165.3 (C=O).

(S,E)-11-[(2-Methylthiazol-5-yl)methylene)hydrazono]-pyrrolo[2,1-c][1,4] Benzodiazepine (4d)

Starting material 2-methylthiazole-5-carboxaldehyde (166.0 mg, 1.305 mmol) was used and the reaction mixture was stirred under nitrogen gas overnight for 15 h. Extraction was performed using chloroform/isopropanol (2:1) (3×20 mL), where the organic layers were dried over anhydrous Na$_2$SO$_4$. The solvent mixture was then removed in vacuo and washed with diethyl ether, filtered off, and dried to afford a yellow solid of 4d. Yield 319.0 mg (72.0%); $^1$H-NMR (400 MHz, DMSO-d$_6$): δ=2.01 (m, 3H), 3.04 (bd, 1H), 3.37 (s, 3H), 3.56 (m, 2H), 4.47 (bd, 1H, H-11a), 7.18 (t, J=7.4 Hz, 1H), 7.36 (d, J=7.4 Hz, 1H), 7.47 (t, J=7.4 Hz, 1H), 7.76 (d, J=7.4 Hz, 1H), 8.17 (s, 1H), 8.23 (s, 1H, CH); $^{13}$C-NMR (100 MHz, DMSO-d$_6$): δ=19.3, 23.8, 26.5, 47.4, 55.7 (C-11a), 122.8, 123.8, 126.9, 128.0, 130.8, 132.3, 137.5, 145.0, 148.6, 158.1, 165.2 (C=O), 172.3.

(S,E)-11-[(4-Methylthiazol-5-yl)methylene)hydrazono]-pyrrolo[2,1-c][1,4] Benzodiazepine (4e)

Starting material 4-methylthiazole-5-carboxaldehyde (122.0 mg, 0.957 mmol) was used and the reaction mixture was stirred under nitrogen gas overnight for 15 h. Extraction was performed using chloroform/isopropanol (2:1) (3×20 mL), where the organic layers were dried over anhydrous Na$_2$SO$_4$. The solvent mixture was then removed in vacuo and washed with diethyl ether, filtered off, and dried to afford an off-white solid of 4e. Yield 198.0 mg (61.0%); $^1$H-NMR (400 MHz, DMSO-d$_6$): δ=2.01 (m, 3H), 3.04 (bd, 1H), 3.37 (s, 3H), 3.56 (m, 2H), 4.47 (bd, 1H, H-11a), 7.18 (m, 1H), 7.36 (m, 1H), 7.47 (m, 1H), 8.25 (s, 1H), 8.67 (s, 1H, CH); $^{13}$C-NMR (100 MHz, DMSO-d$_6$): δ=16.3, 23.5, 26.2, 47.4, 55.8 (C-11a), 122.8, 123.8, 126.9, 128.5, 130.7, 132.3, 137.5, 144.3, 149.2, 155.7, 158.1, 165.3 (C=O).

(S,E)-11-[(2-Aminothiazol-5-yl)methylene)hydrazono]-pyrrolo[2,1-c][1,4] Benzodiazepine (4f)

Starting material 2-aminothiazole-5-carboxaldehyde (64.0 mg, 0.50 mmol) was used and the reaction mixture was stirred under nitrogen gas overnight for 15 h. Extraction was performed using chloroform/isopropanol (2:1) (3×20 mL), where the organic layers were dried over anhydrous Na$_2$SO$_4$. The solvent mixture was then removed in vacuo and washed with diethyl ether, filtered off, and dried to afford an off-white solid of 4f. Yield 115.6 mg (68.0%). $^1$H-NMR (400 MHz, DMSO-d$_6$): δ=2.05 (m, 3H), 3.03 (bs, 1H), 3.56 (m, 2H), 4.43 (bd, 1H, H-11a), 7.14 (t, J=7.5 Hz, 1H), 7.34 (d, J=7.5 Hz, 1H), 7.45 (d, J=7.5 Hz, 1H), 7.73 (d, J=7.5 Hz, 1H), 7.91 (s, 1H, CH), 9.55 (s, 1H, NH); $^{13}$C-NMR (100 MHz, DMSO-d$_6$): δ=23.6, 26.6, 47.2, 55.7 (C-11a), 117.3, 122.5, 123.3, 126.5, 130.7, 132.3, 138.0, 146.6, 148.6, 156.2, 165.4 (C=O), 175.5.

(S,E)-11-[(2,4-Dichlorothiazol-5-yl)methylene)hydrazono]-pyrrolo[2,1-c][1,4]Benzodiazepine (4g)

Starting material 2,4-dichlorothiazole-5-carboxaldehyde (182.0 mg, 1.0 mmol) was used and the reaction mixture was stirred under nitrogen gas overnight for 15 h. Extraction was performed using chloroform/isopropanol (2:1) (3×20 mL), where the organic layers were dried over anhydrous Na$_2$SO$_4$. The solvent mixture was then removed in vacuo and washed with diethyl ether, filtered off, and dried to afford an off-white solid of 4g. Yield 272.0 mg (69.0%); $^1$H-NMR (400 MHz, DMSO-d$_6$): δ=2.01 (m, 3H), 2.89 (bd, 1H), 3.58 (m, 2H), 4.50 (bs, 1H, H-11a), 7.21 (s, 1H), 7.39 (s, 1H), 7.48 (bs, 1H), 7.78 (s, 1H), 8.07 (s, 1H, CH), 10.17 (s, 1H, NH); $^{13}$C-NMR (100 MHz, CDCl$_3$): δ=23.5, 26.8, 47.3, 55.6, 121.9, 123.2, 124.4, 127.2, 130.6, 132.4, 137.1, 139.4, 141.0, 156.6, 160.3, 165.1 (C=O).

(S,E)-11-[2-(Benzo[b]thiophenylmethylene)hydrazono]-pyrrolo[2,1-c][1,4]Benzodiazepine (4h)

Starting material benzo[b]thiophene-2-carbaldehyde (100.0 mg, 0.61 mmol) was used and the reaction mixture was stirred under nitrogen gas overnight for 15 h. Extraction was performed using chloroform/isopropanol (2:1) (3×20 mL). The combined organic layers were dried over anhydrous Na$_2$SO$_4$. The solvent mixture was then removed in vacuo and washed with diethyl ether, filtered off, and dried to afford an off-white solid of 4h. Yield 172.0 mg (75.0%); $^1$H-NMR (400 MHz, CDCl$_3$): δ=2.02-2.07 (m, 3H), 2.98-3.02 (m, 1H), 3.68-3.76 (m, 1H), 3.80-3.87 (m, 1H), 4.39 (d, J=7.6 Hz, 1H, H-11a), 7.04 (d, J=7.3 Hz, 1H), 7.22 (t, J=7.3 Hz, 1H), 7.40 (m, 2H), 7.47 (m, 1H), 7.59 (s, 1H), 7.79-7.86 (m, 2H), 8.00 (d, J=7.6 Hz, 1H), 8.53 (s, 1H, CH), 8.71 (s, 1H, NH); $^{13}$C-NMR (100 MHz, CDCl$_3$): δ=23.5, 25.9, 47.4, 55.4 (C-11a), 120.8, 122.6, 123.9, 124.4, 124.7, 126.2, 126.4, 128.4, 131.4, 132.4, 136.6, 139.4, 139.9, 140.6, 151.6, 157.8, 165.9 (C=O).

(S,E)-11-[(Benzo[b]thiophen-2-ylmethylene)hydrazono]-7-bromo-pyrrolo[2,1-c][1,4]Benzodiazepine (4i)

Starting material benzothiophene-2-carboxaldehyde (81.0 mg, 0.50 mmol) was used and the reaction mixture was stirred under nitrogen gas overnight for 15 h. Extraction was performed using chloroform/isopropanol (2:1) (3×20 mL), where the organic layers were dried over anhydrous Na$_2$SO$_4$. The solvent mixture was then removed in vacuo and washed with diethyl ether, filtered off, and dried to afford an off-white solid of 4i. Yield 158.6 mg (70.0%); $^1$H-NMR (400 MHz, DMSO-d$_6$): δ=2.00 (m, 3H), 2.78 (bs, 1H), 3.58 (m, 2H), 4.48 (bd, 1H, H-11a), 7.41 (m, 1H), 7.68 (dd, J=2.3, 8.8 Hz, 1H), 7.84 (d, J=2.3 Hz, 1H), 7.89 (m, 2H), 7.98 (bd, 1H), 8.75 (s, 1H, CH), 9.31 (s, 1H, NH); $^{13}$C-NMR (100 MHz, DMSO-d$_6$): δ=23.5, 26.3, 47.4, 55.3 (C-11a), 115.5, 123.1, 125.0, 125.1, 125.3, 126.7, 128.4, 129.4, 132.9, 134.9, 137.1, 139.6, 140.2, 140.5, 152.2, 156.4, 164.0 (C=O).

(S,E)-11-[(Benzo[b]thiophen-3-ylmethylene)hydrazono]-7-bromo-pyrrolo[2,1-c][1,4]Benzodiazepine (4j)

Starting material benzothiophene-3-carboxaldehyde (81.0 mg, 0.50 mmol) was used and the reaction mixture was stirred under nitrogen gas overnight for 15 h. Extraction was performed using chloroform/isopropanol (2:1) (3×20 mL), where the organic layers were dried over anhydrous Na$_2$SO$_4$. The solvent mixture was then removed in vacuo and washed with diethyl ether, filtered off, and dried to afford an off-white solid of 4j. Yield 163.0 mg (72.0%).

¹H-NMR (400 MHz, DMSO-d₆): δ=1.97 (m, 3H), 2.83 (bs, 1H), 3.59 (m, 2H), 4.53 (bd, 1H, H-11a), 7.38 (d, J=8.6 Hz 1H), 7.49 (m, 2H), 7.68 (d, J=8.6 Hz, 1H), 7.84 (bs, 1H), 8.06 (d, J=7.5 Hz, 1H), 8.46 (s, 1H), 8.75 (bd, 1H), 8.77 (s, 1H, CH), 9.26 (s, 1H, NH); ¹³C-NMR (100 MHz, DMSO-d₆): δ=23.7, 26.4, 47.6, 55.6 (C-11a), 115.3, 123.3, 125.1, 125.5, 125.6, 125.7, 128.4, 132.1, 132.9, 133.9, 134.9, 136.5, 137.2, 140.4, 152.9, 155.7, 164.1 (C=O).

(S,E)-11-[(Benzo[b]thiophen-2-ylmethylene)hydrazono]-8-chloro-pyrrolo[2,1-c][1,4]Benzodiazepine (4k)

Starting material benzothiophene-2-carboxaldehyde (81.0 mg, 0.50 mmol) was used and the reaction mixture was stirred under nitrogen gas overnight for 15 h. Extraction was performed using chloroform/isopropanol (2:1) (3×20 mL), where the organic layers were dried over anhydrous Na₂SO₄. The solvent mixture was then removed in vacuo and washed with diethyl ether, filtered off, and dried to afford an off-white solid of 4k. Yield 153.0 mg (75.0%); ¹H-NMR (400 MHz, DMSO-d₆): δ=1.99 (m, 3H), 2.79 (bs, 1H), 3.58 (m, 2H), 4.49 (bd, 1H, H-11a), 7.23 (d, J=8.5 Hz, 1H), 7.42 (m, 2H), 7.60 (bs, 1H), 7.77 (d, J=8.5 Hz, 1H), 7.94 (m, 3H), 8.75 (s, 1H, CH), 9.34 (s, 1H, NH); ¹³C-NMR (100 MHz, DMSO-d₆): δ=23.3, 26.3, 47.4, 55.3 (C-11a), 122.1, 123.1, 123.5, 125.0, 125.2, 125.4, 126.6, 129.4, 132.8, 136.5, 138.9, 139.6, 140.3, 140.6, 152.3, 156.3, 164.5 (C=O).

(S,E)-11-[(3-Methylbenzo[b]thiophen-2-yl)methylene)hydrazono]-pyrrolo[2,1-c][1,4]Benzodiazepine (4l)

Starting material 3-methylbenzo[b]thiophene-2-carboxaldehyde (106.0 mg, 0.60 mmol) was used and the reaction mixture was stirred under nitrogen gas overnight for 15 h. Extraction was performed using chloroform/isopropanol (2:1) (3×20 mL), where the organic layers were dried over anhydrous Na₂SO₄. The solvent mixture was then removed in vacuo and washed with diethyl ether, filtered off, and dried to afford a yellow solid of 4l. Yield 152.0 mg (65.0%); ¹H-NMR (400 MHz, DMSO-d₆): δ=2.00 (m, 3H), 2.82 (bs, 1H), 3.37 (s, 3H), 3.58 (m, 2H), 4.44 (bd, 1H, H-11a), 7.19 (t, J=7.0 Hz, 1H), 7.44 (m, 4H), 7.84 (m, 3H), 8.85 (s, 1H, CH), 9.01 (s, 1H, NH); ¹³C-NMR (100 MHz, DMSO-d₆): δ=11.8, 23.5, 26.3, 47.2, 55.3 (C-11a), 122.5, 122.9, 123.1, 123.7, 124.9, 126.6, 126.9, 130.8, 132.5, 134.4, 136.4, 137.4, 139.9, 140.6, 150.6, 156.9, 165.3 (C=O).

(S,E)-11-[(3-Chlorobenzo[b]thiophen-2-yl)methylene)hydrazono]-pyrrolo[2,1-c][1,4]Benzodiazepine (4m)

Starting material 3-chloro-1-benzothiophene-2-carboxaldehyde (98.4 mg, 0.60 mmol) was used and the reaction mixture was stirred under nitrogen gas overnight for 15 h. Extraction was performed using chloroform/isopropanol (2:1) (3×20 mL), where the organic layers were dried over anhydrous Na₂SO₄. The solvent mixture was then removed in vacuo and washed with diethyl ether, filtered off, and dried to afford an off-white solid of 4m. Yield 122.7 mg (60.0%); ¹H-NMR (400 MHz, DMSO-d₆): δ=2.12 (m, 3H), 3.16 (bs, 1H), 3.61 (m, 2H), 4.52 (bd, 1H, H-11a), 7.21 (t, J=7.2 Hz, 1H), 7.39 (m, 1H), 7.54 (m, 2H), 7.78 (d, J=7.2 Hz, 1H), 7.89 (m, 1H), 8.07 (m, 1H), 8.39 (s, 1H, CH), 9.98 (s, 1H, NH); ¹³C-NMR (100 MHz, DMSO-d₆): δ=23.8, 26.9, 47.4, 55.8 (C-11a), 122.5, 122.9, 123.4, 124.0, 124.3, 125.9, 126.2, 127.0, 128.1, 130.8, 132.5, 134.6, 137.4, 140.8, 142.9, 158.9, 165.2 (C=O).

(S,E)-11-[(Benzo[d]thiazol-2-ylmethylene)hydrazono]-pyrrolo[2,1-c][1,4] Benzodiazepine (4n)

Starting material 1,3-benzothiazole-2-carboxaldehyde (142.0 mg, 0.87 mmol) was used and the reaction mixture was stirred under nitrogen gas overnight for 15 h. Extraction was performed using chloroform/isopropanol (2:1) (3×20 mL), where the organic layers were dried over anhydrous Na₂SO₄. The solvent mixture was then removed in vacuo and washed with diethyl ether, filtered off, and dried to afford a yellow solid of 4n. Yield 222.0 mg (68.0%); ¹H-NMR (400 MHz, DMSO-d₆): δ=1.97 (m, 3H), 2.80 (bd, 1H), 3.57 (m, 2H), 4.50 (bd, 1H, H-11a), 7.40 (m, 3H), 7.68 (dd, J=8.9, 2.2 Hz, 1H), 7.84 (d, J=2.2 Hz, 1H), 7.90 (m, 2H), 7.98 (bd, 1H), 8.75 (s, 1H, CH), 9.30 (s, 1H, NH); ¹³C-NMR (100 MHz, DMSO-d₆): δ=23.4, 26.3, 47.4, 55.3 (C-11a), 115.4, 123.1, 124.9, 124.4, 125.2, 126.7, 128.5, 129.4, 132.9, 134.9, 137.0, 139.6, 140.3, 140.6, 152.1, 156.4, 164.0 (C=O).

(S,E)-11-[(1-Methyl-1H-indol-3-yl)methylene)hydrazono]-pyrrolo[2,1-c][1,4]Benzodiazepine (4o)

Starting material 1-methylindole-3-carboxaldehyde (152.0 mg, 0.957 mmol) was used and the reaction mixture was stirred under nitrogen gas overnight for 15 h. The combined organic layers were dried over anhydrous Na₂SO₄. The solvent mixture was then removed in vacuo and washed with diethyl ether, filtered off, and dried to afford a yellow solid of 4o. Yield 244.0 mg (69.0%); ¹H-NMR (400 MHz, DMSO-d₆): δ=1.98 (m, 3H), 2.87 (bs, 1H), 3.36 (s, 3H), 3.58 (m, 2H), 4.45 (bs, 1H, H-11a), 7.23 (m, 3H), 7.34 (bd, 1H), 7.51 (m, 2H), 7.78 (d, J=8.0 Hz, 1H), 7.92 (s, 1H), 8.38 (d, J=8.0 Hz, 1H), 8.65 (s, 1H, CH), 8.98 (s, 1H, NH); ¹³C-NMR (100 MHz, DMSO-d₆): δ=23.5, 26.2, 33.3, 47.3, 55.5 (C-11a), 55.6, 110.6, 111.7, 121.4, 122.3, 122.9, 123.1, 125.6, 126.4, 130.9, 132.4, 132.5, 135.8, 138.0, 138.1, 153.3, 154.7, 165.5 (C=O).

(S,E)-11-[(5-Methoxy-1H-indol-3-yl)methylene)hydrazono]-pyrrolo[2,1-c][1,4]Benzodiazepine (4p)

Starting material 5-methoxy-1-methylindole-3-carbaldehyde (100.0 mg, 0.57 mmol) was used and the reaction mixture was stirred under nitrogen gas overnight for 15 h. Extraction was performed using chloroform/isopropanol (2:1) (3×20 mL). The combined organic layers were dried over anhydrous Na₂SO₄. The solvent mixture was then removed in vacuo and washed with diethyl ether, filtered off, and dried to afford a brown solid of 4p. Yield 153.0 mg (68.0%); ¹H-NMR (400 MHz, DMSO-d₆): δ=1.99 (m, 3H), 2.84 (bs, 1H), 3.37 (s, 3H), 3.60 (m, 2H), 4.47 (bs, 1H, H-11a), 6.84 (bd, 1H), 7.14 (bt, 1H), 7.34 (m, 2H), 7.49 (bt, 1H), 7.77 (bd, 1H), 7.80 (d, J=2.4 Hz, 1H), 7.89 (d, J=2.4 Hz, 1H), 8.67 (s, 1H, CH), 9.01 (s, 1H, NH); ¹³C-NMR (100 MHz, DMSO-d₆): δ=23.6, 26.2, 47.4, 55.4 (C-11a), 55.6, 104.0, 112.4, 112.9, 113.0, 121.7, 123.0, 125.8, 126.0, 131.0, 132.3, 132.4, 132.6, 138.1, 153.7, 154.6, 154.9, 165.5 (C=O).

(S,E)-11-[(Adamantan-1-yl)methylene)hydrazono]-pyrrolo[2,1-c][1,4] Benzodiazepine (4q)

Starting material adamantane-1-carboxaldehyde (164.0 mg, 1.0 mmol) was used and the reaction mixture was stirred under nitrogen gas overnight for 15 h. Extraction was performed using chloroform/isopropanol (2:1) (3×20 mL), where the organic layers were dried over anhydrous $Na_2SO_4$. The solvent mixture was then removed in vacuo and washed with diethyl ether, filtered off, and dried to afford a yellow solid of 4q. Yield 256.0 mg (68.0%); $^1$H-NMR (400 MHz, $CDCl_3$): δ=1.74 (m, 11H), 2.01 (m, 7H), 2.91 (bd, 1H), 3.75 (m, 2H), 4.29 (bd, 1H, H-11a), 6.95 (d, J=9.5 Hz, 1H), 7.15 (t, J=8.4 Hz, 1H), 7.41 (t, J=7.4 Hz, 1H), 7.95 (d, J=8.4 Hz, 1H), 8.40 (s, 1H, CH); $^{13}$C-NMR (100 MHz, $CDCl_3$): δ=23.4, 26.0, 27.9, 36.7, 37.3, 39.7, 47.3, 50.6, 55.3 (C-11a), 120.6, 123.5, 126.1, 131.3, 132.3, 136.9, 156.9, 166.1, 168.9 (C=O).

Cannabinoid Receptor Binding Assay

The affinities of the compounds for CB1 and CB2 receptors were examined using displacement assays, as previously described. Briefly, cell membranes from CHO cells expressing human CB1 or human CB2 receptors were isolated using differential centrifugation. Test compounds reconstituted in DMSO and were incubated with the isolated membrane in binding buffer (50 mM Tris-HCl, 1 mM EDTA, 3 mM MgCl2, 5 mg/mL BSA, pH 7.4) along with 2.5 nM [$^3$H]CP-55,940. Total binding was assessed in the presence of equal concentration of DMSO, while non-specific binding was determined in the presence of 10 μM CP-55, 940, and background binding was determined in wells lacking membrane. Following incubation at 30° C. for 60 min, the binding reactions were terminated by vacuum filtration through Whatman GF/C filters. The filters were then washed twice with ice-cold buffer (50 mM Tris-HCl, 1 mg/mL BSA). Liquid scintillation cocktail was added to each well and the total tritiated counts per minute were analyzed using a TopCount scintillation counter. Background counts were subtracted from all wells and the percent displacement from total binding was calculated.

The compounds were initially screened at 10 μM concentrations. If they produced at least ±30% displacement of the radioligand, then full competition curves were constructed. $K_i$ values were calculated using GraphPad Prism (San Diego, CA, USA) and $K_d$ values determined using a 1 site fit. All assays were run in technical and biological replicates so that the n=5-6. PK Evaluation in CD-1 Mice
Preparation of Stock Solutions, Calibration Standards, Quality Control Samples and Internal Standard Solution The primary stock solutions of 4k and phenacetin (internal standard, IS) were prepared in methanol at a concentration of 1.0 mg/mL. Working solutions of calibration standards and quality control (QC) samples were prepared by dilution with methanol and stored at −20° C. A working stock of the IS solution (20 ng/mL) was prepared in methanol and stored at −20° C.
Instrument and Analytical Conditions Chromatography was performed on an Acquity™ UPLC system (Waters Corp, Milford, MA, USA) with an autosampler temperature at 10° C. Waters Acquity UPLC® HSS C18 column (3.0×50 mm, 1.8 μm particle size) was used for chromatographic separation with linear gradient elution consisting of (A) 90% acetonitrile and (B) 10% 0.2% formic acid in Milli-Q water as mobile phases. The flow rate was set at 0.30 mL/min, and the injection volume was 2 μL.

An Acquity Tandem Quadrupole Mass Detector (Xevo TQ-S; Waters Corp, Milford, MA, USA) in positive electrospray ionization mode was used for mass spectrometric detection. For collision-induced dissociation, argon was used as collision gas. The cone voltage and collision energy were set at 60 V and 34 V for 4k and 46 V and 26 V for the IS, respectively. Quantification was performed using the monitoring of multiple reaction monitoring (MRM) of following transitions: m/z 409.0/220.9 for 4k and m/z 180.0/92.7 for IS. Retention times of 4k and IS were 2.85 and 1.81 min, respectively.
Sample Preparation A simple protein precipitation method was followed for extraction of 4k from mice plasma. To an aliquot of 50 μL of plasma or tissue (brain, liver, or kidney) samples, IS solution (5 μL of 20 ng/mL) was added and mixed for 15 s on a cyclomixer (Thermo Scientific, Indianapolis, IN, USA). After precipitation with 200 μL of acetonitrile, the mixture was vortexed for 2 min, followed by centrifugation for 10 min at 14,000 rpm on an accuSpin Micro 17R (Fisher Scientific, Suwanee, GA, USA) at 5° C. An aliquot of ~150 μL of clear supernatant was transferred into vials and 2 μL was injected onto LC-MS/MS system for analysis.
In Vivo Studies in CD-1 Mice All work involving animal subjects was pre-approved by the University of Mississippi Institutional Animal Care and Use Committee and was conducted in accordance with ethical guidelines defined by the National Institutes of Health (NIH Publication No. 85-23).
Subjects Male CD-1 mice (N=48) were obtained from Envigo (St. Louis, MO, USA) and maintained on a 12:12 h reversed dark/light cycle (lights off at 07:00 h) with ad libitum access to food and water. Following a ~4 h fast, animals were randomly assigned to one of two groups. Group I and II animals (n=24/group, weight range 25-30 g) received compound 4k (5 mg/kg) orally (in the form of a solution, prepared using 10% absolute alcohol, 10% cremophor, and 80% Milli-Q water) or intravenously (i.v., using solution formulation comprising 10% absolute alcohol, 10% cremophor, and 80% normal saline), respectively. At 0.5, 1, 2, 4, 8, and 24 h post administration, animals were euthanized, blood was collected in K2. EDTA-containing polypropylene tubes and, tissues were collected (brain, liver, and kidney). Plasma was harvested by centrifuging the blood using Eppendorf 5430R Centrifuge (Germany) at 5000 rpm for 5 min and stored frozen at −80° C. until analysis.
Tissue Preparation Brain, liver, and kidney tissues were homogenized in separate 15 mL round-bottom screw-capped vials in phosphate buffered saline (5 volumes of each tissue mass) with a homogenizer (Polytron®) and stored at −80° C. until analysis. Plasma or tissue homogenates (50 μL) were spiked with IS and processed as mentioned in sample preparation section.
Pharmacokinetic Assessments Plasma and tissue concentration and time data of compound 4k were analyzed by a non-compartmental method using WinNonlin Version 5.3 (Pharsight Corporation, Mountain View, CA, USA).

Example 2: Results and Discussion

Chemistry

To gain a better understanding of the structure-activity relationships of 4, the range of PBD-11-hydrazinyl derivatives (4a-4q) was extended by alkenylation of the primary amine group of the cycloamidine 3 via the formation of a Schiff's base with various carboxaldehydes. Synthetic approaches were initiated based on the stepwise synthesis of dilactam 1 by the cyclocondensation of an equimolar mixture of L-proline and readily available basic structure of PBD natural product, isatoic anhydride (or substituted compound) in DMF at 155° C. Thionation of compound 1 with 0.5 eq. of 2,4-bis-(4-methoxyphenyl)-1,3-dithia-2,4-diphosphetane-2,4-disulfide (Lawesson's reagent) in THF at room temperature produced thiolactam 2. The subsequent treatment of 2 with 98% hydrazine monohydrate in ethanol at room temperature generated cycloamindine 3. The title compound 3 was further subjected to condensation with several aldehydes in anhydrous MeOH and molecular sieves (3 Å) at room temperature to afford a cluster of highly conjugated Schiff's base 4 in high yield. This procedure involves the initial formation of the intermediate carbinol amine, which dehydrates to form an imine. The reaction time was varied from a few minutes to a couple of hours and gave the desired products in good yields. The alkenylation of 3 with aldehydes was best performed under optimized conditions in which the parent molecule was exposed to five equivalents of aldehyde in methanol for varied reaction times at room temperature. Upon further crystallization of crude product from EtOAc/hexanes, pure (S,E)-11-[2-(arylmethylene)hydrazono]-PBD analogs (4a-4q) were formed as crystalline solids. The chemical structures are shown in Table 1. These compounds are structurally unique from any reported small-molecule CB ligands, confirming the chemotype novelty of all the generated compounds.

TABLE 1

Selected Compounds, Structures, and Yields

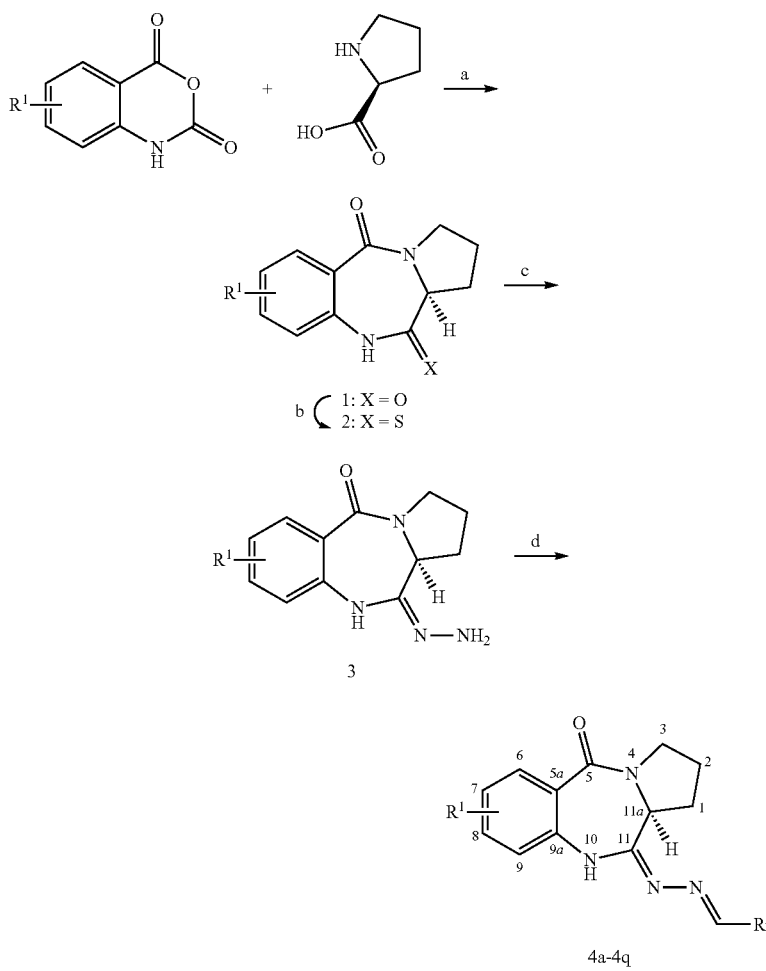

| Compound | $R^1$ | $R^2$ | Yield (%) |
|---|---|---|---|
| (S,E)-11-[(1H-Pyrrol-2-yl)methylene)hydrazono]-pyrrolo[2,1-c][1,4]Benzodiazepine (4a) | H | pyrrol-2-yl | 62 |
| (S,E)-11-[(1-Methyl-1H-imidazol-2-yl)methylene)hydrazono]-pyrrolo[2,1-c][1,4]Benzodiazepine (4b) | H | 1-methyl-1H-imidazol-2-yl | 65 |

TABLE 1-continued

Selected Compounds, Structures, and Yields

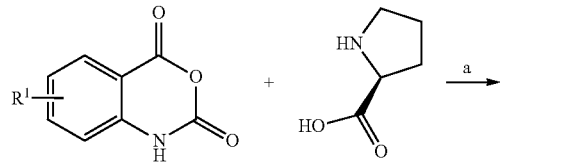

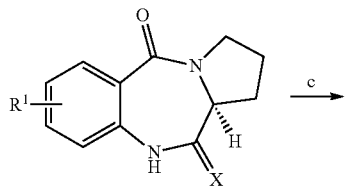

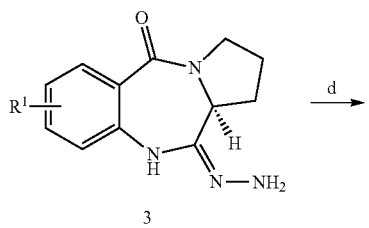

4a-4q

| Compound | R¹ | R² | Yield (%) |
|---|---|---|---|
| (S,E)-11-[(Thiazol-5-ylmethylene)hydrazono]-pyrrolo[2,1-c][1,4]Benzodiazepine (4c) | H | thiazol-5-yl | 71 |
| (S,E)-11-[(2-Methylthiazol-5-yl)methylene)hydrazono]-pyrrolo[2,1-c][1,4]Benzodiazepine (4d) | H | 2-methylthiazol-5-yl | 72 |
| (S,E)-11-[(4-Methylthiazol-5-yl)methylene)hydrazono]-pyrrolo[2,1-c][1,4]Benzodiazepine (4e) | H | 4-methylthiazol-5-yl | 61 |
| (S,E)-11-[(2-Aminothiazol-5-yl)methylene)hydrazono]-pyrrolo[2,1-c][1,4]Benzodiazepine (4f) | H | 2-aminothiazol-5-yl | 68 |

TABLE 1-continued

Selected Compounds, Structures, and Yields

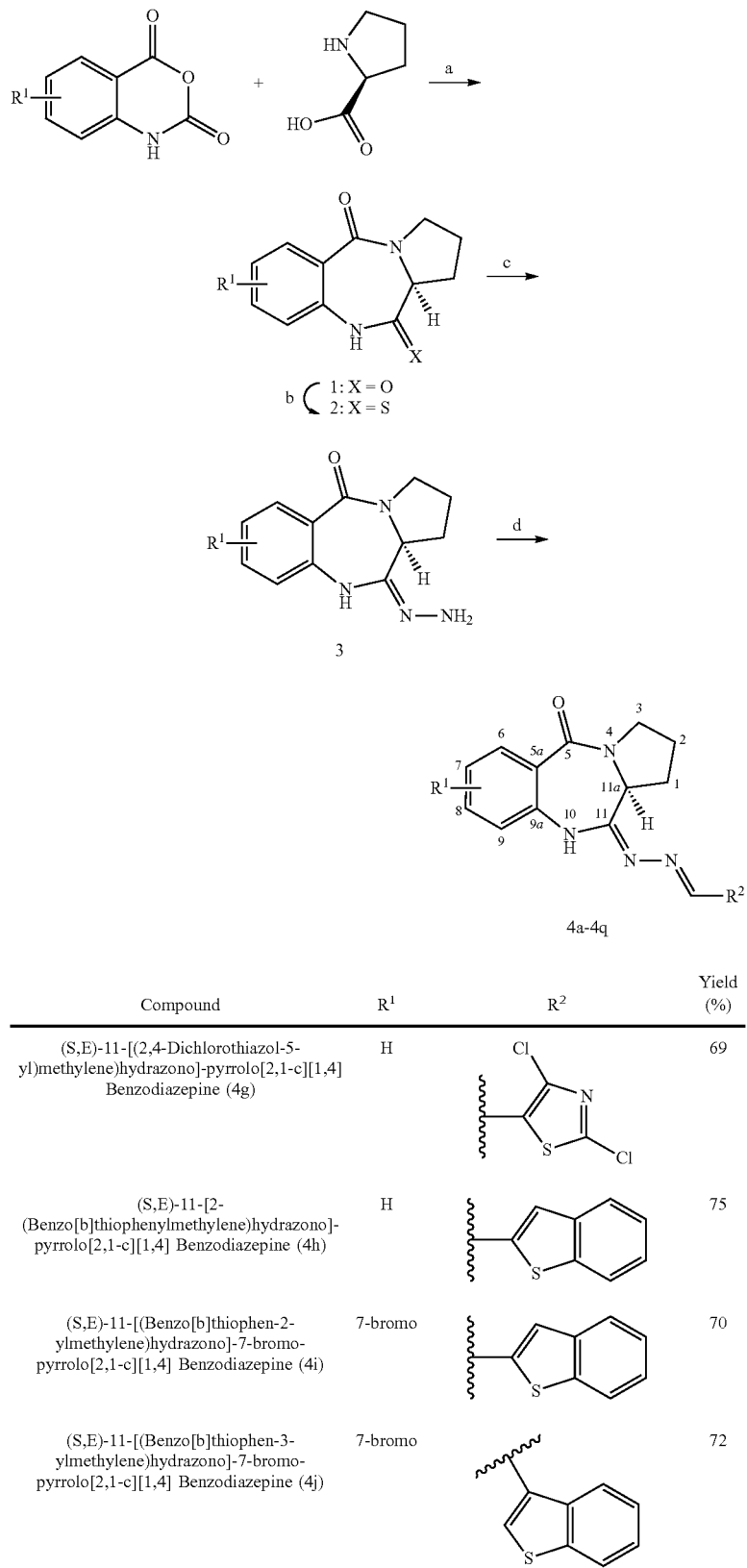

| Compound | R[1] | R[2] | Yield (%) |
|---|---|---|---|
| (S,E)-11-[(2,4-Dichlorothiazol-5-yl)methylene)hydrazono]-pyrrolo[2,1-c][1,4] Benzodiazepine (4g) | H | 2,4-dichlorothiazol-5-yl | 69 |
| (S,E)-11-[2-(Benzo[b]thiophenylmethylene)hydrazono]-pyrrolo[2,1-c][1,4] Benzodiazepine (4h) | H | benzo[b]thiophen-2-yl | 75 |
| (S,E)-11-[(Benzo[b]thiophen-2-ylmethylene)hydrazono]-7-bromo-pyrrolo[2,1-c][1,4] Benzodiazepine (4i) | 7-bromo | benzo[b]thiophen-2-yl | 70 |
| (S,E)-11-[(Benzo[b]thiophen-3-ylmethylene)hydrazono]-7-bromo-pyrrolo[2,1-c][1,4] Benzodiazepine (4j) | 7-bromo | benzo[b]thiophen-3-yl | 72 |

TABLE 1-continued

Selected Compounds, Structures, and Yields

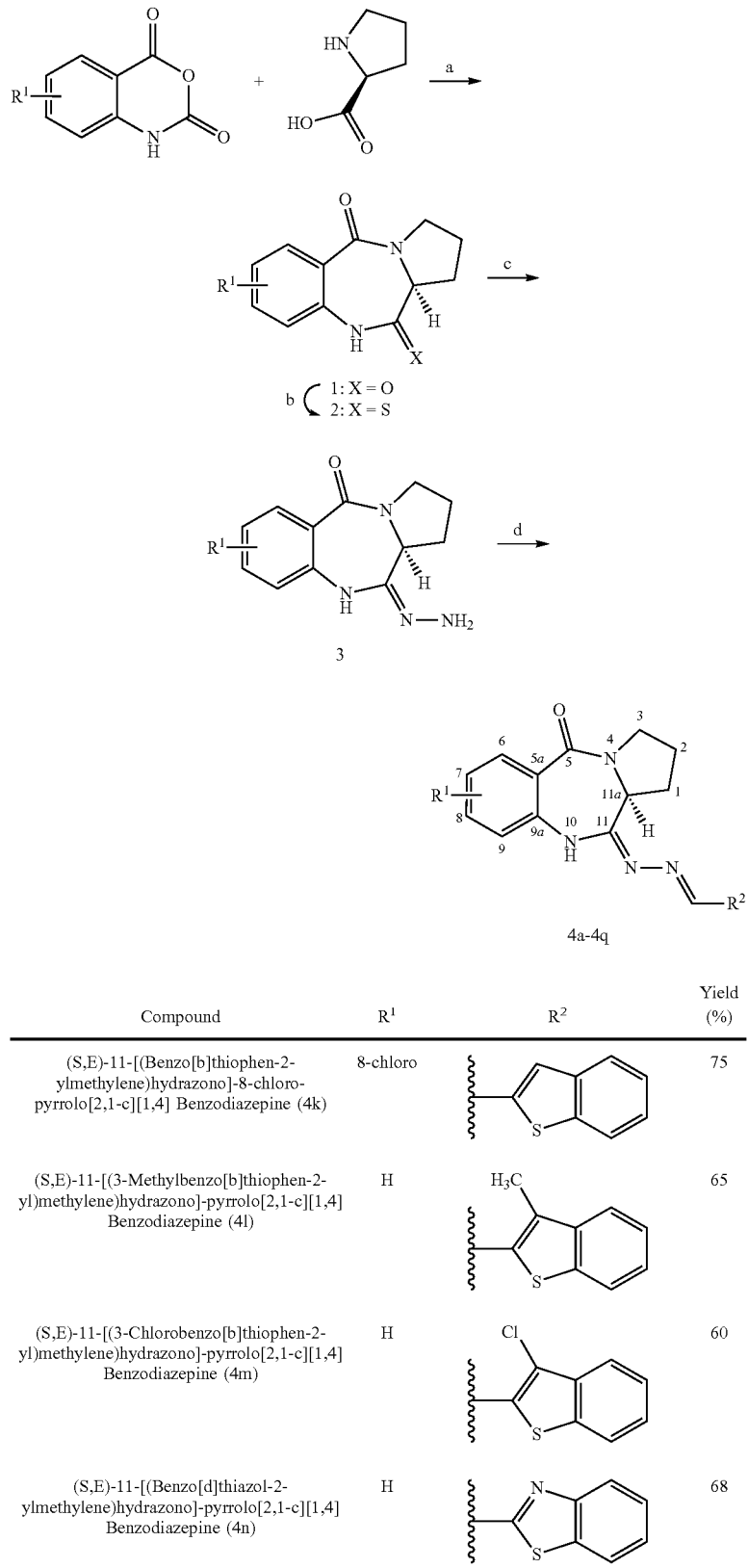

| Compound | R[1] | R[2] | Yield (%) |
|---|---|---|---|
| (S,E)-11-[(Benzo[b]thiophen-2-ylmethylene)hydrazono]-8-chloro-pyrrolo[2,1-c][1,4] Benzodiazepine (4k) | 8-chloro | | 75 |
| (S,E)-11-[(3-Methylbenzo[b]thiophen-2-yl)methylene)hydrazono]-pyrrolo[2,1-c][1,4] Benzodiazepine (4l) | H | | 65 |
| (S,E)-11-[(3-Chlorobenzo[b]thiophen-2-yl)methylene)hydrazono]-pyrrolo[2,1-c][1,4] Benzodiazepine (4m) | H | | 60 |
| (S,E)-11-[(Benzo[d]thiazol-2-ylmethylene)hydrazono]-pyrrolo[2,1-c][1,4] Benzodiazepine (4n) | H | | 68 |

TABLE 1-continued

Selected Compounds, Structures, and Yields

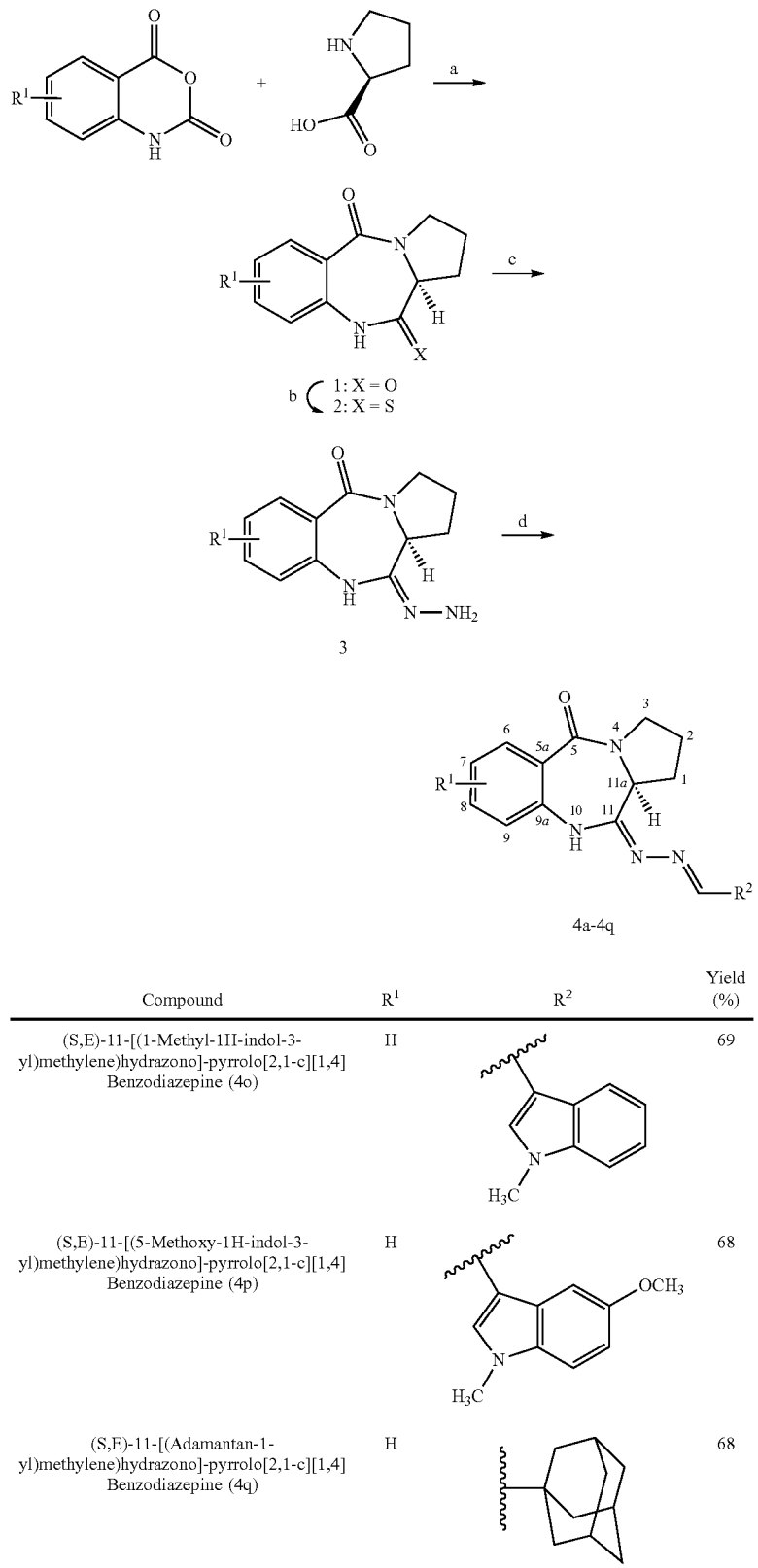

| Compound | R¹ | R² | Yield (%) |
|---|---|---|---|
| (S,E)-11-[(1-Methyl-1H-indol-3-yl)methylene)hydrazono]-pyrrolo[2,1-c][1,4] Benzodiazepine (4o) | H | | 69 |
| (S,E)-11-[(5-Methoxy-1H-indol-3-yl)methylene)hydrazono]-pyrrolo[2,1-c][1,4] Benzodiazepine (4p) | H | | 68 |
| (S,E)-11-[(Adamantan-1-yl)methylene)hydrazono]-pyrrolo[2,1-c][1,4] Benzodiazepine (4q) | H | | 68 |

Reagents and conditions: (a) DMF, 155° C., 5 h, 82.0%; (b) Lawesson's reagent, THF, rt, 15 h, 87.0%; (c) $N_2H_4$—$H_2O$ (98%), EtOH(abs.), rt, 15 h, 99.0%; (d) Aldehydes, MeOH (anhy.), rt, 15 h, 60-75.0%.

Biological Evaluation of the Synthesized Compounds
Cannabinoid Receptors Displacement Assay The CB1/CB2 receptor binding activities of analogs 4a-4q were assessed via radioactivity-based competitive binding assays using [$^3$H]CP55,940, an extensively studied radioligand that is frequently used for cannabinoid assays. The highly potent and nonselective CB agonist CP55,940 binds to the same orthosteric active site where known CB agonists are known to bind. In preliminary screening, all 17 synthetic PBD compounds (4a-4q) were subjected to in vitro CB1 and CB2 binding assays at a single concentration of 10 µM. The observed percentage displacement (%) of the radioligand at the CB receptors of these analogs are summarized in Table 2. From the 17 compounds evaluated in the competitive radioligand assay, compounds 4h, 4j-4l, and 4q showed significant displacement (more than 60%). Among them, two structurally distinct PBD analogs (4k and 4q) displayed the greatest [$^3$H]CP-55,940 displacement and selectivity for CB2 over CB1. Therefore, the most promising ligands (4k and 4q) were selected for assessment in full competition curves against CB1 and CB2. The binding assays revealed selective binding affinity of 4k and 4q with $K_i$ values of 146 and 137 nM, respectively, toward CB2 receptors (Table 3).

TABLE 2

Displacement of [$^3$H]CP-55,940 from CB1 and CB2 receptors by 10 µM concentration of compounds 4a-4q.

| Compound | CB1(%) | CB2(%) |
|---|---|---|
| 4a | −3.09 | −12.50 |
| 4b | −13.99 | −14.48 |
| 4c | 0.25 | 3.06 |
| 4d | −27.99 | −33.65 |
| 4e | 21.88 | 19.86 |
| 4f | 1.75 | 3.72 |
| 4g | 24.19 | 29.27 |
| 4h | 36.88 | 61.05 |
| 4i | 49.82 | 36.39 |
| 4j | 66.81 | 65.24 |
| 4k | 41.26 | 84.60 |
| 4l | 77.17 | 51.73 |
| 4m | 5.22 | 50.05 |
| 4n | 44.14 | 43.34 |
| 4o | 5.09 | 1.01 |
| 4p | −27.20 | −29.47 |
| 4q | 55.27 | 95.58 |

TABLE 3

Cannabinoid Receptor Binding Assays of the Lead Compounds against CB2

| Compound | Structure | $K_i$ (nM) |
|---|---|---|
| 4k | (structure) | 146 |
| 4q | (structure) | 137 |

In Vivo PK Studies of the Lead Analog 4k

Drug discovery research programs routinely execute mouse PK studies to characterize the PK properties of compounds as a filtering tool to advance drug candidates through the pipeline as well as to support efficacy and toxicology studies. Stability studies on two selected analogs has revealed a better tolerance of 4k under physiological pH when compared to 4q compound (not reported). Consequently, 4k was selected for pharmacokinetic studies in CD1 male mice at 5 mg/kg body weight (Table 4, FIGS. 2A-2D).

TABLE 4

Pharmacokinetic parameters of compound 4k in CD1 mice following intravenous and oral dosing of 4k in mice at 5 mg/kg.

| PK Parameters | | Intravenous | | | | Oral | | | |
|---|---|---|---|---|---|---|---|---|---|
| | | Plasma | Brain | Kidney | Liver | Plasma | Brain | Kidney | Liver |
| $t_{1/2}$ | h | 6.91 | 6.54 | 10.2 | 9.26 | 16.4 | 22.9 | 16.7 | 13.0 |
| $C_{max}$ Or $C_0$ | ng/ml or ng/g | 4345 | 2260 | 4725 | 13497 | 198 | 602 | 795 | 1891 |
| $T_{max}$ | h | — | — | — | — | 0.88 | 1.25 | 0.75 | 0.75 |
| $AUC_{0-\infty}$ | ng × h/mL or ng × h/g | 4015 | 5685 | 13272 | 19991 | 739 | 3.69 | 5223 | 6423 |
| CL | mL/min/kg | 23.5 | 15.7 | 6.38 | 4.28 | — | — | — | — |
| $V_d$ | L/kg | 14.3 | — | — | — | — | — | — | — |
| F | % | — | — | — | — | 18 | 43 | 37 | 32 |

$t_{1/2}$: half-life; $C_{max}$: maximum concentration; $C_0$: plasma concentration estimated at time 0 for IV; $T_{max}$: time at maximum concentration at 0.5 h; $AUC_{0-\infty}$: area under the curve to infinite time; CL: clearance; $V_d$: volume of distribution; F: bioavailability.

In plasma, the concentrations of compound 4k decreased in a mono-exponential manner after 5.0 mg/kg intravenous administration. The mean clearance (CL) was found to be 23.5±5.35 mL/min/kg, which is 26% of hepatic blood flow in mice. Compound 4k had a high volume of distribution of 14.3±3.11 L/kg. The terminal half-life (t1/2) was found to be 6.91±0.15 h. The post oral administration, maximum plasma concentrations ($C_{max}$: 198±11.51 ng/mL) were attained at 0.88±0.13 h ($T_{max}$), indicating rapid absorption from the gastrointestinal tract. The apparent half-life (16.4±1.66 h) determined after oral administration was longer than that after intravenous administration (6.91 h), which may indicate multiple sites of absorption. The AUC0-∞ attained post oral dose was 739±6.75 ng×h/mL. The oral bioavailability in mice at 5 mg/kg was 18±2.43% (Table 4).

In the brain, the concentrations of compound 4k decreased mono-exponentially after 5.0 mg/kg intravenous administration. The mean brain clearance (CL) was found to be 15.7±2.31 mL/min/kg. Compound 4k had a high volume of distribution of 8.82±2.43 L/kg in the brain. The terminal half-life (t1/2) was found to be 6.54±1.38 h. Post oral administration, the maximum brain concentrations ($C_{max}$: 602±44.75 ng/g) were attained at 1.25±0.44 h ($T_{max}$). The apparent half-life was found to be 22.9±3.73 h. The AUC0-∞ attained post oral dose was 3069±64 ng×h/g. The apparent oral bioavailability to the brain, as compared to IV administration, was 42.5±5.75% (Table 2). The mean brain to plasma ratios after intravenous and oral administration were 3.67 and 4.61, respectively, which indicates that the compound had very good brain penetration.

In the kidney, the concentrations of compound 4k decreased mono-exponentially after 5.0 mg/kg intravenous administration. The mean kidney clearance (CL) was found to be 6.38±0.49 mL/min/kg. Compound 4k had a high volume of distribution of 5.63±0.37 L/kg in the kidney. The terminal half-life (t1/2) was found to be 10.2±0.49 h. Post oral administration, the maximum kidney concentrations ($C_{max}$: 795±22.65 ng/g) were attained at 0.75±0.15 h ($T_{max}$). The apparent half-life was found to be 16.7±1.61 h. The $AUC_{0-\infty}$ attained post oral dose was 5223±44.75 ng×h/g. The apparent oral bioavailability in the kidney at 5 mg/kg was 37±3.78% (Table 2). The mean kidney to plasma ratios after intravenous and oral administration were 14.5 and 7.25, respectively.

In the liver, the mean liver clearance (CL) was found to be 4.28±0.38 mL/min/kg. Compound 4k had a high volume of distribution of 3.38±0.18 L/kg in liver. The terminal half-life (t1/2) was found to be 9.26±0.67 h. Post oral administration, the maximum liver concentrations ($C_{max}$: 1891±282 ng/g) were attained at 0.75±0.15 h ($T_{max}$). The apparent half-life was found to be 13.0±0.97 h. The $AUC_{0-\infty}$ attained post oral dose was 6423±571 ng x h/g. The apparent oral bioavailability in the liver at 5 mg/kg was 32±2.86% (Table 2). The mean liver to plasma ratios after intravenous and oral administration were 11.5 and 9.89, respectively.

Conclusion

Through a structure-based rational drug design, a subset of 17 (S,E)-11-[2-(arylmethylene)hydrazono]-PBD derivatives was synthesized using a multi-step synthesis approach to establish clusters of highly potent and selective CB2 ligands. Most of the designed analogs exhibited a high percentage displacement (%) of the CB1 and CB2 receptor. Most importantly, the most promising compounds, 4k and 4q, displayed sub-micromolar efficacy ($K_i$ of 146 and 137 nM) when tested for in a binding affinity assay.

Previous studies have shown suitable drug-like properties of this class of ligands via the computational calculation of ADMET and physicochemical properties. The reported data validated that almost all the designed analogs possess Abs_risk, CYP_Risk, TOX_Risk, and ADMET_Risk within the satisfactory defined limits. The current pharmacokinetics assessments further support the favorable drug-like behavior of this class in that the oral bioavailability is reasonable and tissue uptake, especially brain penetration, is high, with a prolonged half-life. This suggests the feasibility of central nervous system activity with simple dose regimens. The structure-activity relationships (SAR) suggested that attachment of S-heterocyclic aldehydes (e.g., benzothiophene) to the hydrazine portion, in addition to an 8-chloro-substituted PBD, improves the selectivity of CB2 over CB1. Moreover, the adamantyl pharmacophore establishes extensive hydrophobic interactions with three phenylalanine residues and one histidine residue within the active site of the CB2 receptor. Most notably, these bioactive compounds represent structurally new chemotypes in the area of cannabinoid research and could be considered for further structural optimization as selective CB2 ligands.

Example 3: Acetic Acid-Induced Writhing Tests

Figure 3A:
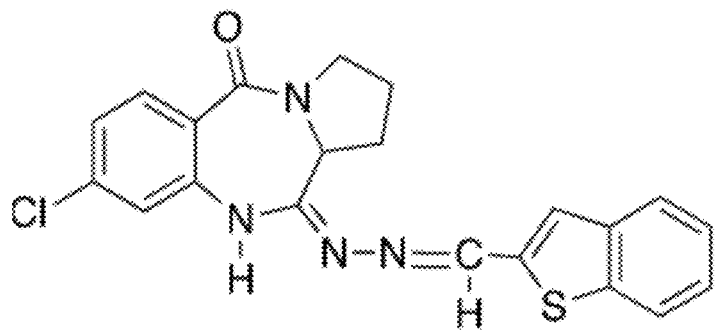
FIGS. 3A-3B show results of treatment of mice with disclosed compound 4k compared to oxycodone or vehicle. In a 30-minute acetic acid writhing test, either oxycodone (dark gray bars) or compound 4k (light gray bars) attenuate writhing compared to vehicle administration (black bars) indicating analgesia to a model of visceral pain. Data are shown in 5 min bins (FIG. 3A) and as total writhing activity over 30 mins.
Figure 3A:
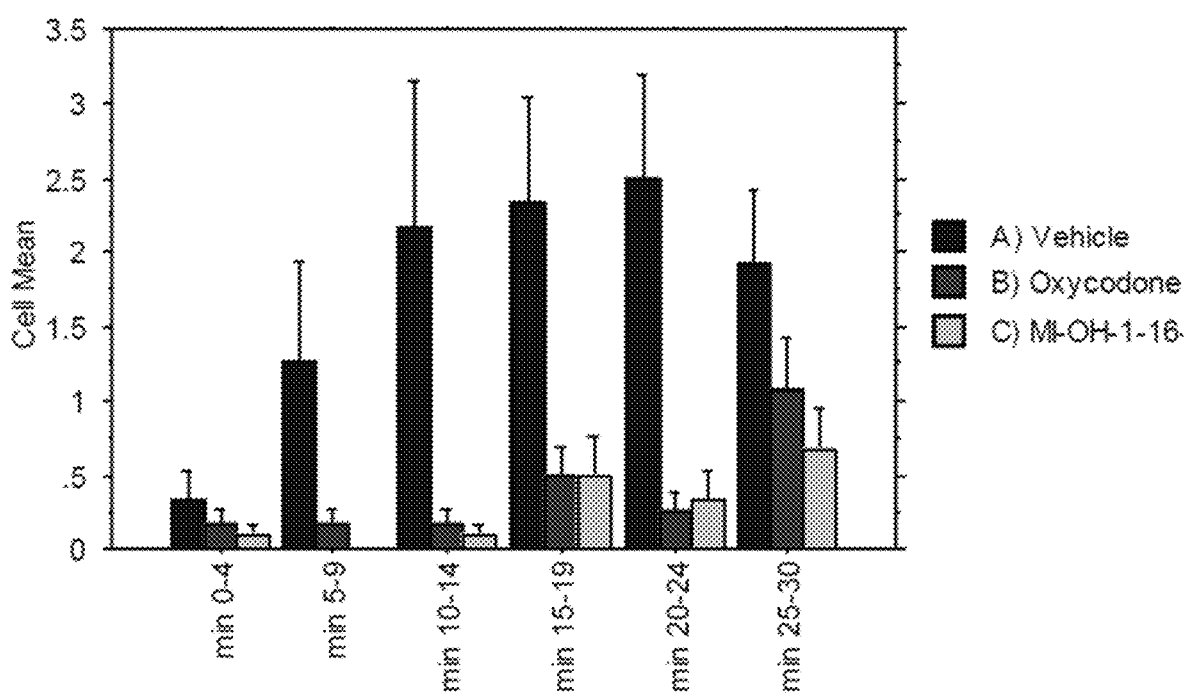
Figure 3B:
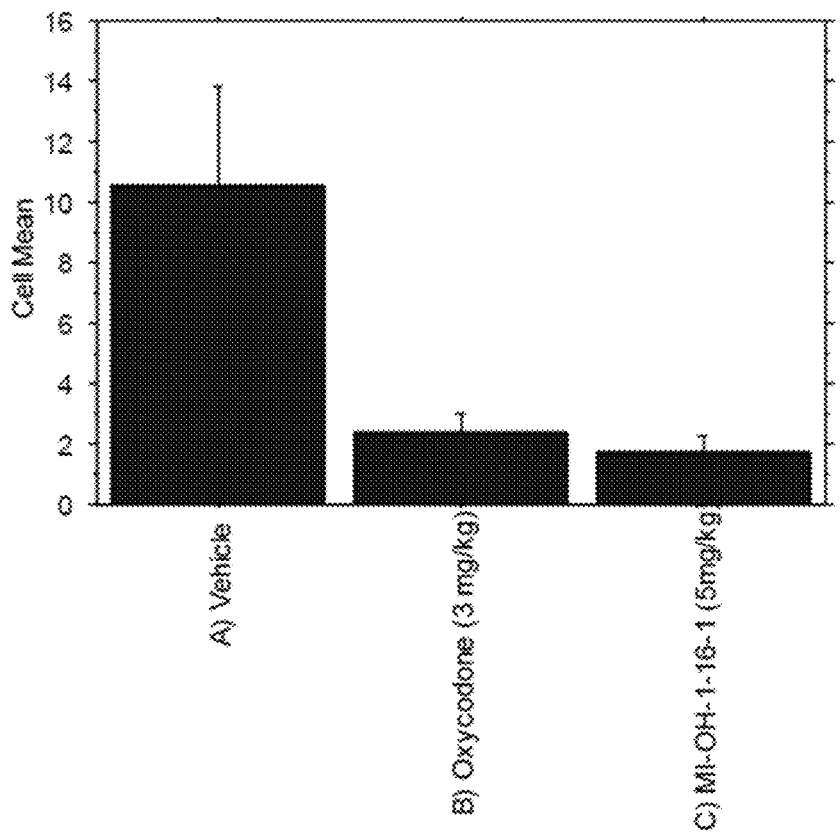

Acetic acid-induced writhing is widely used for assessing analgesic effects against inflammatory pain of peripheral origin. Analgesic activity of the disclosed compound was demonstrated as a decrease in the frequency of writhing as described in the literature. Writhing was monitored over 30 minutes for mice treated with vehicle, oxycodone (3 mg/kg), and compound 4k (5 mg/kg), with compound 4k treated mice showing significantly less writhing (an index of visceral pain) than other groups across all time points. Results are presented in FIGS. 3A-3B. FIG. 3A shows that the number writhes per 5 min. were lower for compound 4k treated mice than for untreated (vehicle) mice and were commensurate to those for oxycodone-treated mice at the same time points. FIG. 3B shows that total frequency of writhes over the entire experiment were lowest for compound 4k treated mice, commensurate with oxycodone-treated mice.

Example 4: Conditioned Place Preference Testing

Figure 4:
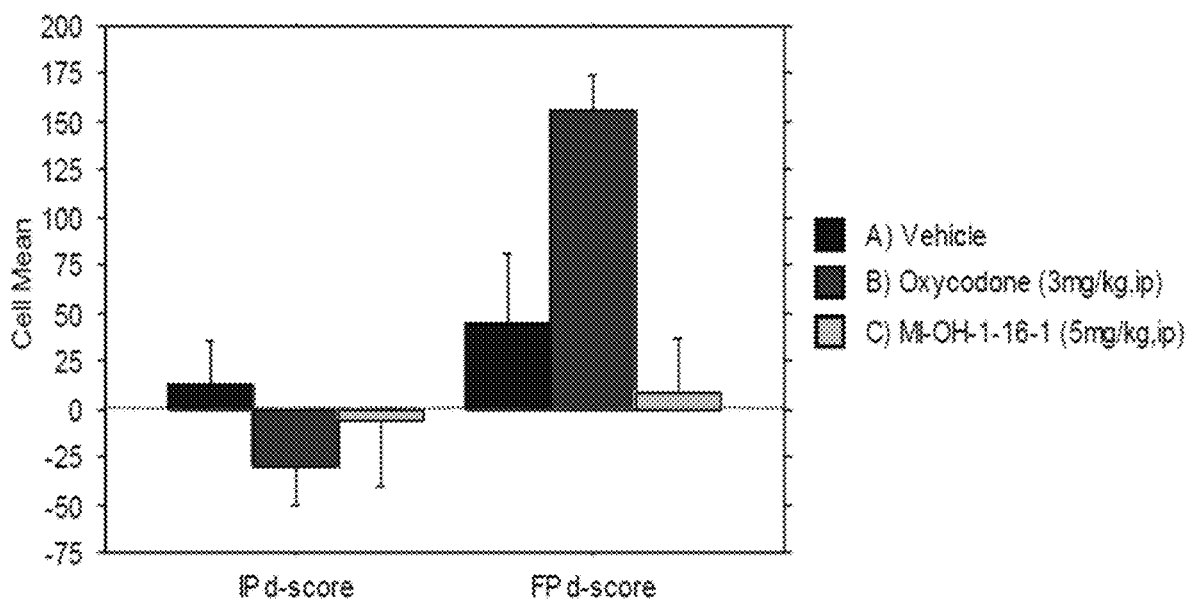
FIG. 4. Shows the results of a conditioned place preference test which demonstrates that compound 4k (light gray bars) exerts no significant rewarding effects, unlike that observed for oxycodone (dark gray bars), supporting the notion that 4 k lacks the abuse liability of oxycodone IP=initial preference, FP=final preference, d-score=difference score (indicating the difference in time spent on the drug-paired side from the vehicle-paired side of the conditioned place preference apparatus).

Conditioned place preference testing is used to assess a compound's rewarding effects in order to gauge potential abuse liability. Mice are "conditioned" to associate distinctly lighted/colored/textured chambers with a rewarding drug (e.g., opioid) or no drug. If the mice sense a rewarding effect of the drug, they will prefer to occupy the chamber associated with that drug. FIG. 4 presents the results of a conditioned place preference test for 3 groups of mice (i.e., vehicle, oxycodone treated, and compound 4k treated). Mice treated with oxycodone, an opioid drug, showed a clear place preference for the rewarding effect chamber. However, mice treated with 4k showed no such preference, suggesting no rewarding effect, and thus limited abuse liability compared to oxycodone.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Beltramo, M.; Bernardini, N.; Bertorelli, R.; Campanella, M.; Nicolussi, E.; Fredduzzi, S.; Reggiani, A. CB2 receptor-mediated antihyperalgesia: Possible direct involvement of neural mechanisms. Eur. J. Neurosci. 2006, 23, 1530-1538.
2. Brettschneider, J.; Tredici, K. D.; Lee, V. M.; Trojanowski, J. Q. Spreading of pathology in neurodegenerative diseases: A focus on human studies. Nat. Rev. Neurosci. 2015, 16, 109-120.
3. Cipolla, L.; AraOjo, A. C.; Airoldi, C.; Bini, D. Pyrrolo[2,1-c][1,4]benzodiazepine as a scaffold for the design and synthesis of anti-tumour drugs. Anticancer Agents Med. Chem. 2009, 9, 1-31.
4. Dean, B.; Sundram, S.; Bradbury, R.; Scarr, E.; Copolov, D. Studies on [3H]CP-55940 binding in the human central nervous system: Regional specific changes in density of cannabinoid-1 receptors associated with schizophrenia and *cannabis* use. Neuroscience 2001, 103, 9-15.
5. Gao, H. M.; Hong, J. S. Why neurodegenerative diseases are progressive: Uncontrolled inflammation drives disease progression. Trends Immunol. 2008, 29, 357-365.
6. Hebert, L. E.; Weuve, J.; Scherr, P. A.; Evans, D. A. Alzheimer disease in the United States (2010-2050) estimated using the 2010 census. Neurology 2013, 80, 1778-1783.
7. Jayant, S.; Sharma, B. M.; Bansal, R.; Sharma, B. Pharmacological benefits of selective modulation of cannabinoid receptor type 2 (CB2) in experimental Alzheimer's disease. Pharmacol. Biochem. Behav. 2016, 140, 39-50.
8. Klein, T. W. Cannabinoid-based drugs as anti-inflammatory therapeutics. Nat. Rev. Immunol. 2005, 5, 400-411.
9. Li, X.; Hua, T.; Vemuri, K.; Ho, J. H.; Wu, Y.; Wu, L.; Popov, P.; Benchama, O.; Zvonok, N.; Qu, L.; et al. Crystal structure of the human cannabinoid receptor CB2. Cell 2019, 176, 459-467.
10. McPartland, J. M. Phylogenomic and chemotaxonomic analysis of the endocannabinoid system. Brain Res. Rev. 2004, 45, 18-29.
11. Mingle, D.; Ospanov, M.; Radwan, M. O.; Ashpole, N.; Otsuka, M.; Ross, S. A.; Walker, L.; Shilabin, A. G.; Ibrahim, M. A. First In Class (S,E)-11-[2-(Arylmethylene)Hydrazono]-PBD Analogs As Selective CB2 Modulators Targeting Neurodegenerative Disorders. Med. Chem. Res. 2020, 1-11.
12. Mukhopadhyay, S.; Das, S.; Williams, E. A.; Moore, D.; Jones, J. D.; Zahm, D. S.; Ndengele, M. M.; Lechner, A. J.; Howlett, A. C. Lypopolysaccharide and cyclic AMP regulation of CB2 cannabinoid receptor levels in rat brain and mouse RAW 264.7 macrophages. J. Neuroimmunol. 2006, 181, 82-92.
13. Nakagawa, Y.; Chiba, K. Role of microglial m1/m2 polarization in relapse and remission of psychiatric disorders and diseases. Pharmaceuticals 2014, 7, 1028-1048.
14. Schmidt, A.; Shilabin, A. G.; Namyslo, J. C.; Nieger, M.; Hemmen, S. Pyrimidine-annulated Pyrrolobenzodiazepines. A New Ring System Related to *Aspergillus* Alkaloids. Eur. J. Org. Chem. 2005, 1781-1789.
15. Schmidt, A.; Shilabin, A. G.; Nieger, M. Syntheses and tautomerization of amino-substituted and pyrimidine-annulated pyrrolobenzodiazepines. Heterocycles 2005, 65, 625-632.
16. Stempel, A. V.; Stumpf, A.; Zhang, H. Y.; Ozdogan, T.; Pannasch, U.; Theis, A. K.; Otte, D. M.; Wojtalla, A.; Racz, I.; Ponomarenko, A.; et al. Cannabinoid type 2 receptors mediate a cell type-specific plasticity in the hippocampus. Neuron 2016, 90, 795-809.
17. Wu, J.; Bie, B.; Yang, H.; Xu, J. J.; Brown, D. L.; Naguib, M. Activation of the CB2 receptor system reverses amyloid-induced memory deficiency. Neurobiol. Aging 2013, 34, 791-804.

What is claimed is:

1. A compound comprising a structure of Formula I:

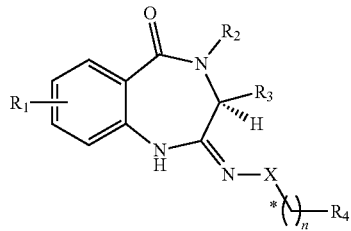

Formula I wherein $R_1$ is selected from hydrogen, halogen, hydroxy, substituted or unsubstituted $C_1$-$C_{10}$ alkyl, substituted or unsubstituted $C_1$-$C_{10}$ alkoxy, aryl, nitro, or cyano;

wherein $R_2$ and $R_3$ are independently selected from hydrogen, halogen, aryl, substituted or unsubstituted $C_1$-$C_{10}$ alkyl, or wherein $R_2$ and $R_3$ are connected to form a $C_2$-$C_{10}$ alkyl chain;

wherein $R_4$ is selected from

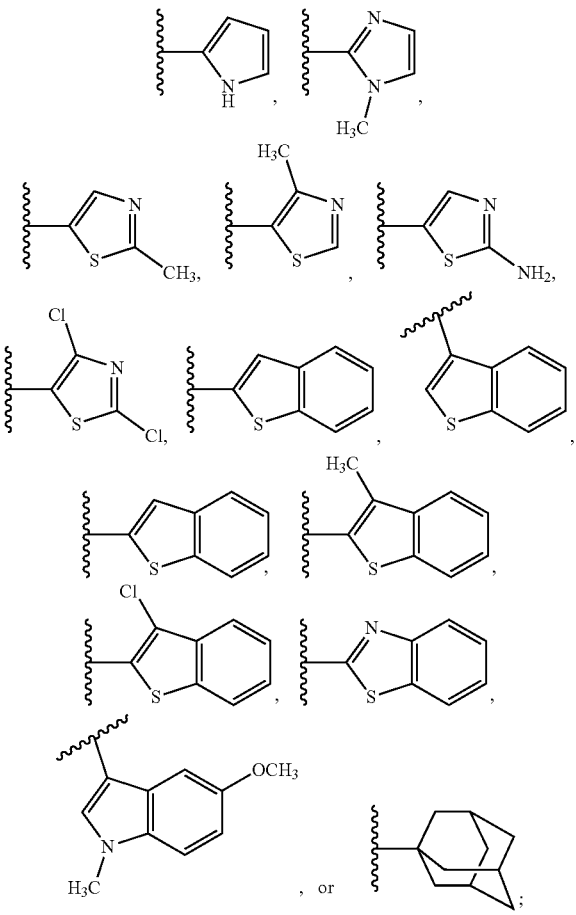

, or wherein X is selected from O, S, N, NH, CH, CH$_2$, or CO;
wherein n is from 0 to 10;
and wherein a bond indicated by * is a double bond or a single bond based on a valence of X.

2. The compound of claim 1, wherein the compound is selected from Formula Ia or Formula Ib Formula Ia
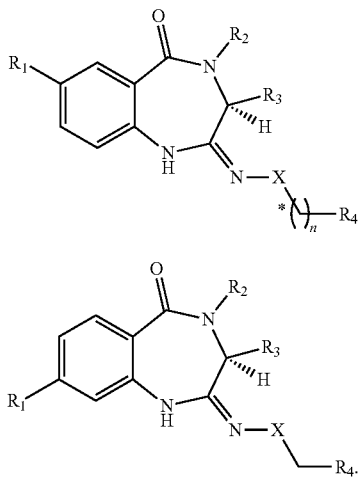

Formula Ib

3. The compound of claim 2, wherein R$_1$ is selected from H, bromine, or chlorine.

4. The compound of claim 1, wherein R$_2$ and R$_3$ are connected to form a C$_2$-C$_{10}$ alkyl chain.

5. The compound of claim 4, wherein the compound has Formula Ic

Formula Ic
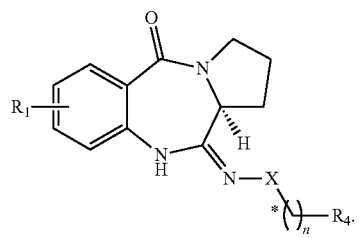

6. The compound of claim 1, wherein X is N and wherein the bond indicated by * is a double bond.

7. The compound of claim 1, wherein n is 1.

8. The compound of claim 1, wherein the compound has the structure

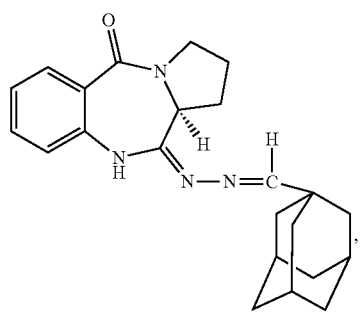

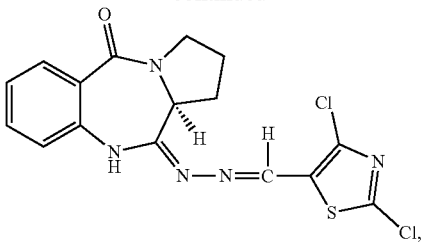

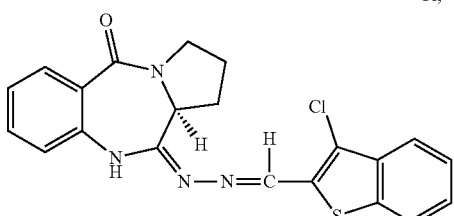

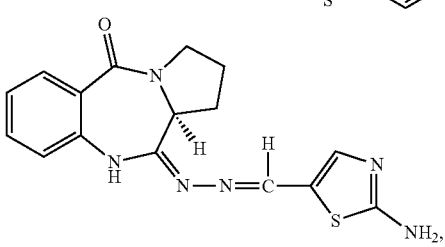

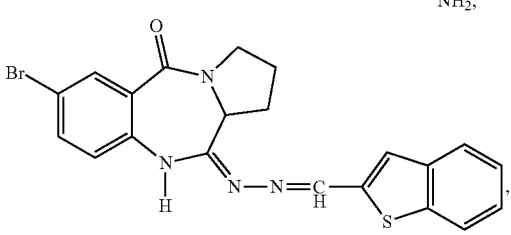

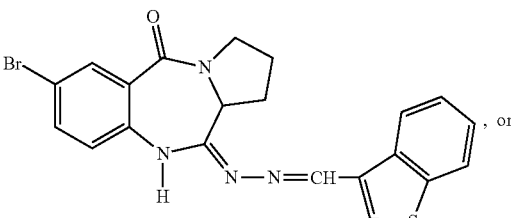

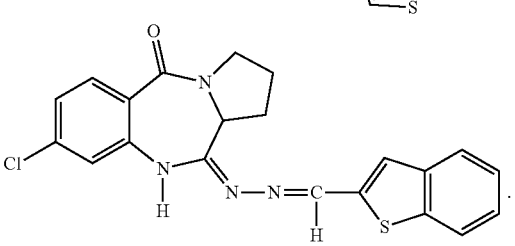

combination thereof.

9. A pharmaceutical composition comprising the compound of claim 1 or a pharmaceutically acceptable salt thereof.

10. A method for treating pain or a neurological disorder, the method comprising administering a therapeutically effective amount of the pharmaceutical composition of claim 9 to a subject.

11. The method of claim 10, wherein the neurological disorder comprises Alzheimer's disease, Parkinson's disease, multiple sclerosis, or any combination thereof.

12. The method of claim 10, wherein the pain comprises pain resulting from an injury, pain resulting from a pain disorder, post-surgical pain, pain resulting from an infection, or any combination thereof.

13. The method of claim 10, wherein the compound is administered orally or intravenously.

14. The method of claim 10, wherein the compound penetrates the blood-brain barrier.

15. The method of claim 10, wherein the compound or pharmaceutically acceptable salt has an in vivo half-life of greater than about 20 hours.

16. The method of claim 10, wherein the compound or pharmaceutically acceptable salt binds to CB2.

17. The method of claim 16, wherein the compound has a $K_i$ for CB2 of less than about 150 nM.

18. The method of claim 16, wherein the compound is at least about 1.5 times more selective for CB2 over CB1.

19. The method of claim 10, wherein administering the compound to the subject does not result in the subject becoming addicted to the compound.

* * * * *